United States Patent
Roetzschke et al.

(10) Patent No.: US 9,213,028 B2
(45) Date of Patent: Dec. 15, 2015

(54) METHOD AND KIT FOR RAPID ISOLATION OF HUMAN FOXP3+ TREG CELLS

(71) Applicant: Max-Delbruck-Centrum fur Molekulare Medizin (MDC), Berlin (DE)

(72) Inventors: Olaf Roetzschke, Singapore (SG); Kirsten Falk, Berlin (DE); Markus Kleinewietfeld, Berlin (DE)

(73) Assignee: MAX-DELBRUCK-CENTRUM FUR MOLEKULARE MEDIZIN (MDC), Berlin (DE)

( * ) Notice: Subject to any disclaimer, the term of this patent is extended or adjusted under 35 U.S.C. 154(b) by 0 days.

(21) Appl. No.: 14/089,179

(22) Filed: Nov. 25, 2013

(65) Prior Publication Data

US 2014/0080150 A1    Mar. 20, 2014

Related U.S. Application Data

(63) Continuation-in-part of application No. 12/682,674, filed as application No. PCT/EP2008/008599 on Oct. 10, 2008, now abandoned.

(30) Foreign Application Priority Data

| Oct. 12, 2007 | (EP) | .................................. 07020026 |
| Dec. 20, 2007 | (EP) | .................................. 07024782 |
| Apr. 4, 2008 | (EP) | .................................. 08006864 |
| Apr. 30, 2008 | (EP) | .................................. 08008255 |

(51) Int. Cl.

| C12N 5/071 | (2010.01) |
| G01N 33/535 | (2006.01) |
| G01N 33/569 | (2006.01) |
| C12N 5/0783 | (2010.01) |
| A61K 35/12 | (2015.01) |

(52) U.S. Cl.
CPC ........ *G01N 33/56972* (2013.01); *C12N 5/0636* (2013.01); *A61K 2035/122* (2013.01)

(58) Field of Classification Search
None
See application file for complete search history.

(56) References Cited

U.S. PATENT DOCUMENTS

| 6,017,719 A | 1/2000 | Tseng-Law et al. | ......... 435/7.21 |
| 2005/0164387 A1 | 7/2005 | Flyer et al. | .................... 435/372 |
| 2008/0131445 A1 | 6/2008 | Bluestone et al. | ......... 424/184.1 |

FOREIGN PATENT DOCUMENTS

WO    WO 2007/014420 A1    2/2007

OTHER PUBLICATIONS

Allan et al. "Activation-induced FOXP3 in Human T Effector Cells Does Not Suppress Proliferation or Cytokine Production" International Immunology 2007 vol. 19(4): 345-354.
Baecher-Allan, C. and Hafler, D. A. "Human Regulatory T Cells and Their Role in Autoimmune Disease" Immunological Reviews 2006 vol. 212: 203-216.
Baecher-Allan et al. "CD4+CD25high Regulatory Cells in Human Peripheral Blood" The Journal of Immunology 2001 vol. 167: 1245-1253.
Barnard et al. "Engagement of Specific T-Cell Surface Molecules Regulates Cytoskeletal Polarization in HTLV-1-Infected Lymphocytes" Blood 2005 vol. 106(3): 988-995.
Beyer, M. and Schultze, J.L. "CD4+CD25$^{high}$FOXP3+ Regulatory T Cells in Peripheral Blood Are Primarily of Effector Memory Phenotype" Journal of Clinical Oncology 2007 25:2628-2630, 3903.
Borsellino et al. "Differential Expression of VLA-4 by Functional Treg and Effector CD4+ T-Cells" Clinical Immunology 2006 vol. 119: S84.
Dieckmann et al. "Ex Vivo Isolation and Characterization of CD4$^+$CD25$^+$ T Cells with Regulatory Properties from Human Blood" Journal of Experimental Medicine 2001 vol. 193(11): 1303-1310.
Ebert, L. M. and McColl, S. R. "Coregulation of CXC Chemokine Receptor and CD4 Expression on T Lymphocytes During Allogeneic Activation" The Journal of Immunology 2001 vol. 166: 4870-4878.
Fontenot et al. "A Function for Interleukin 2 in Foxp3-expressing Regulatory T Cells" Nature Immunology 2005 vol. 6(11): 1142-1151 With "Erratum: A Function for Interleukin 2 in Foxp3-expressing Regulatory T Cells" Nature Immunology 2006 vol. 7(4): 427.
Fontenot et al. "Regulatory T Cell Lineage Specification by the Forkhead Transcription Factor Foxp3"Immunity 2005 vol. 22: 329-341.
Fontenot, J. D. and Rudensky, A. Y. "A Well Adapted Regulatory Contrivance: Regulatory T Cell Development and the Forkhead Family Transcription Factor Foxp3" Nature Immunology 2005 vol. 6(4): 331-337.
Hartigan-O'Connor et al. "Human CD4+ Regulatory T Cells Express Lower Levels of the IL-7 Receptor Alpha Chain (CD127), Allowing Consistent Identification and Sorting of Live Cells" Journal of Immunological Methods 2007 vol. 319: 41-52.
Hoffmann et al. "Isolation of CD4$^+$CD25$^+$ Regulatory T Cells for Clinical Trials" Biology of Blood and Marrow Transplantation 2006 vol. 12: 267-274.
Hori et al. "Control of Regulatory T Cells Development by the Transcription Factor *Foxp3*" Science 2003 vol. 299: 1057-1061.

(Continued)

*Primary Examiner* — Amy Juedes
(74) *Attorney, Agent, or Firm* — Licata & Tyrrell P.C.

(57) ABSTRACT

The present invention relates to methods for isolating human forkhead box P3 (Foxp3+) CD4+ regulatory T cells (herein referred to a Foxp3+ Treg cells) from a sample containing (i) peripheral blood mononuclear cells (PBMCs), (ii) a lymphocyte containing fluid, or (iii) a lymphocyte containing tissue, a kit for isolating human Foxp3+ Treg cells, and the use of anti-CD49d antibody for the isolation of human Foxp3+ Treg cells.

8 Claims, 9 Drawing Sheets

(56) References Cited

OTHER PUBLICATIONS

Huehn et al. "Developmental Stage, Phenotype, and Migration Distinguish Naive- and Effector/Memory-like CD4+ Regulatory T Cells" The Journal of Experimental Medicine 2004 vol. 199(3): 303-313.

Kleinewietfeld, M. "Charakterisierung von CD25+ Regulatorischen T Zellen" Dissertation, Freie Universität Berlin, Pharmazie 2006 Http://www.diss.fu-berlin.de/dis/receive/FUDISS_thesis_000000003036>.

Kleinewietfeld et al. "CCR6 Expression Defines Regulatory Effector/Memory-like Cells within the $CD25_+CD4^+$ T-cell Subset" Blood 2005 vol. 105(7): 2877-2886.

Kleinwietfeld et al. "OR.34. Rapid Isolation of 'Untouched' Human Foxp3+ Treg Cells" Clinical Immunology 2008 vol. 127: S15.

Kleinewietfeld et al. "CD49d Provides Access to 'Untouched' Human Foxp3+ Treg Free of Contaminating Effector Cells" Blood 2009 vol. 113(4): 827-836.

Kohm et al. "Cutting Edge: Anti-CD25 Monoclonal Antibody Injection Results in the Functional Inactivation, Not Depletion, of CD4+CD25+ T Regulatory Cells" The Journal of Immunology 2006 vol. 176: 3301-3305.

Liu et al. "CD127 Expression Inversely Correlates with FoxP3 and Suppressive Function of Human CD4+ T Reg Cells" The Journal of Experimental Medicine 2006 vol. 203(7): 1701-1711.

Masteller et al. "Expansion of Functional Endogenous Antigen-Specific CD4+CD25+ Regulatory T Cells from Nonobese Diabetic Mice" The Journal of Immunology 2005 vol. 175:3053-3059.

McNeill et al. "Partial Depletion of $CD69^{low}$—expressing Natural Regulatory T Cells with the Anti-CD25 Monoclonal Antibody PC61" Scandinavian Journal of Immunology 2007 vol. 65: 63-69.

Mischke et al. "Investigation of the Regulatory Function of CD4+/CD25high T Cells in Cell Culture Models with Human PBMC" Immunobiology 2005 vol. 210: 403.

Mutis et al. "Human Regulatory T Cells Control Xenogeneic Graft-versus-Host Disease Induced by Autologous T Cells in $RAG2^{-/-}\gamma c^{-/-}$ Immunodeficient Mice" Clinical Cancer Research 2006 vol. 12(18): 5520-5525.

Randolph, D. A. and Fathman, C. G. "CD4+CD25+ Regulatory T Cells and Their Therapeutic Potential" Annual Review of Medince 2006 vol. 57: 381-402.

Robinson et al. "Tregs and Allergic Disease" The Journal of Clinical Investigation 2004 vol. 114(10): 1389-1397.

Roncarolo, M. and Battaglia, M. "Regulatory T-Cell Immunotherapy for Tolerance to Self Antigens and Alloantigens in Humans" Nature Reviews Immunology 2007 vol. 7: 585-598.

Safarik, I. and Safarikova, M. "Use of Magnetic Techniques for the Isolation of Cells" Journal of Chromatography B 1999 722:33-53.

Sakaguchi, S. "Naturally Arising CD4+ Regulatory T Cells for Immunologic Self-Tolerance and Negative Control of Immune Responses" Annual Review of Immunology 2004 vol. 22: 531-562.

Seddiki et al. "Expression of Interleukin (IL)-2 and IL-7 Receptors Discriminates Between Human Regulatory and Activated T Cells" The Journal of Experimental Medicine 2006 vol. 203(7):1693-1700.

Sharpe, A. H. and Abbas, A. K. "T-Cell Costimulation-Biology, Therapeutic Potential, and Challenges" The New England Journal of Medicine 2006 vol. 355(10): 973-975.

Sharpe, P. T. "Methods of Cell Separation" Laboratory Techniques in Biochem and Molecular Biology 1988 18: 1-272.

Stassen et al. "Human $CD25_+$ Regulatory Cells: Two Subsets Defined by the Integrins $a_4\beta_7$ or $a_4\beta_1$ Confer Distinct Suppressive Properties Upon CD4+ T Helper Cells" European Journal of Immunology 2004 vol. 34: 1303-1311.

Suntharalingam et al. "Cytokine Storm in a Phase 1 Trial of the Anti-CD28 Monoclonal Antibody TGN1412" The New England Journal of Medicine 2006 vol. 355(10): 1018-1028.

Tang, Q. and Bluestone, J. A. "Regulatory T-cell Physiology and Application to Treat Autoimmunity" Immunological Reviews 2006 212:217-237.

Thornton et al. "Cutting Edge: IL-2 is Critically Required for the In Vitro Activation of CD4+CD25+ T Cell Suppressor Function" The Journal of Immunology 2004 vol. 172: 6519-6523.

von Bonin et al. "Dipeptidyl-peptidase IV/CD26 on T Cells: Analysis of an Alternative T-cell Activation Pathway" Immunological Reviews 1998 161:43-53.

Waldmann et al. "Regulatory T Cells and Organ Transplantation" Seminars in Immunology 2004 vol. 16: 119-126.

Office Communication dated Mar. 25, 2013 from U.S. Appl. No. 12/682,674, filed Sep. 23, 2010.

Office Communication dated Jul. 24, 2013 from U.S. Appl. No. 12/682,674, filed Sep. 23, 2010.

Office Communication dated Oct. 10, 2013 from U.S. Appl. No. 12/682,674, filed Sep. 23, 2010.

International Search Report From PCT/EP2008/008599, Feb. 18, 2009, PCT.

International Preliminary Report on Patentability from PCT/EP2008/008599, Apr. 13, 2010, PCT.

Search Report from Singapore Application No. 201002426-3, Nov. 3, 2011, Singapore.

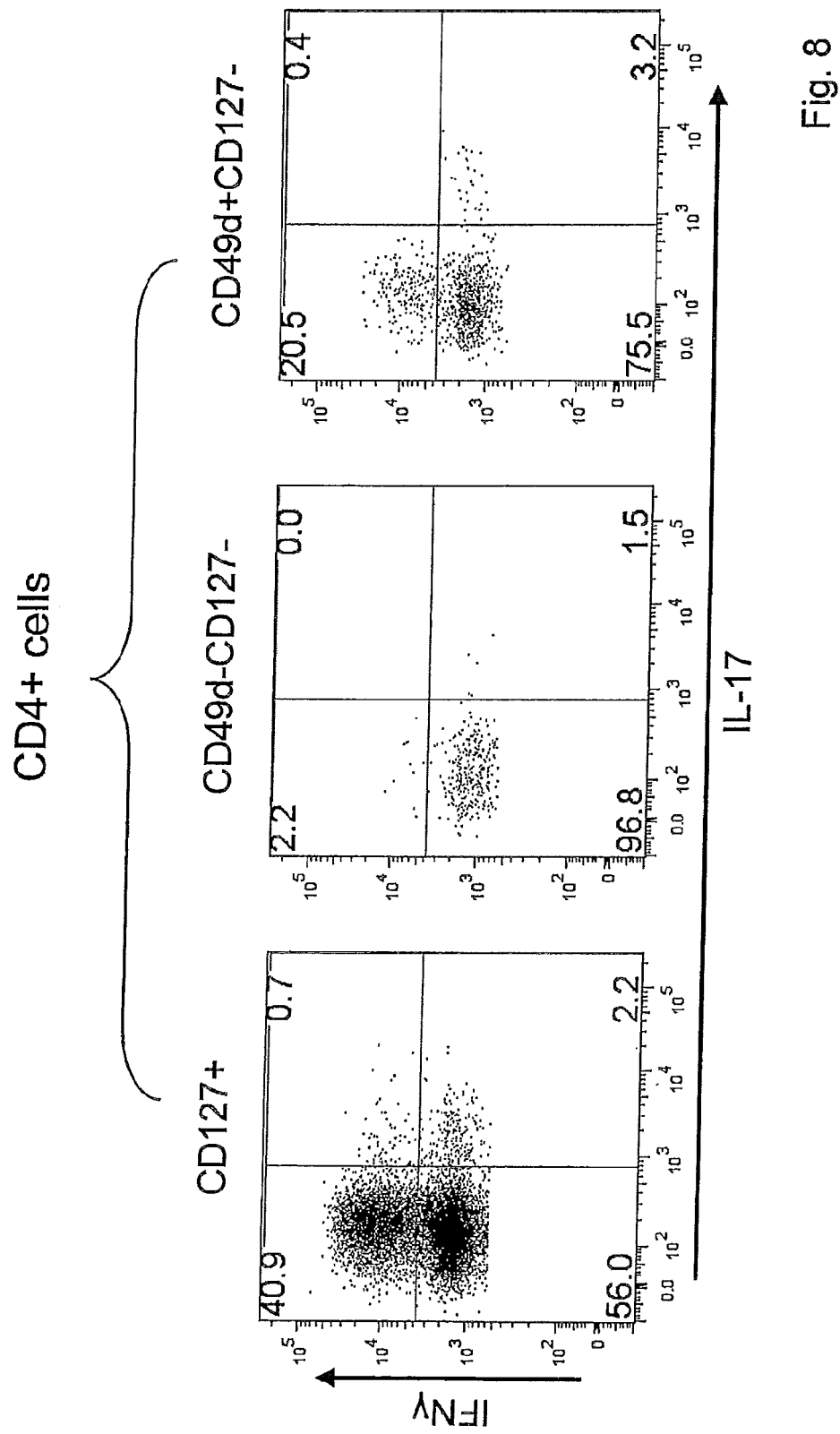

METHOD AND KIT FOR RAPID ISOLATION OF HUMAN FOXP3+ TREG CELLS

INTRODUCTION

This application is a continuation application of U.S. patent application Ser. No. 12/682,674, filed Sep. 23, 2010, which is the national stage under 35 U.S.C. §371 of PCT International Application No. PCT/EP2008/008599, filed Oct. 10, 2008, which claims priority from EP 07020026.6, filed Oct. 12, 2007; EP 07024782.0, filed Dec. 20, 2007; EP 08006864.6, filed Apr. 4, 2008; and EP 08008255.5, filed Apr. 30, 2008, the contents of which are incorporated herein by reference in their entireties.

BACKGROUND

Foxp3+ regulatory T cells, or 'Tregs' are fundamental in controlling various immune responses in that Tregs can rapidly suppress the activity of other immune cells. In particular, Tregs are crucial for maintaining tolerance by downregulating undesired immune responses to self and non-self antigens (see, e.g. Fontenot, J. D. & Rudensky, A. Y. *Nat Immunol* 6, 331-7 (2005); Sakaguchi, S., *Annu Rev Immunol* 22, 531-62 (2004)). For instance, Treg defects have been discovered in patients with multiple sclerosis (MS), type I diabetes (T1D), psoriasis, myasthenia gravis (MG) and other autoimmune diseases (Baecher-Allan, C. & Hafler, D. A., *Immunol Rev* 212, 203-16 (2006)). Similar links may also exist for atopy and allergic diseases (Robinson, D. S., Larche, M. & Durham, S. R., *J Clin Invest* 114, 1389-97 (2004)). For all these diseases reports exist pointing to a reduced in vitro immune suppression of the patient's Treg cells. This has led to an increasing interest in the possibility of using Tregs in immunotherapy to treat or prevent chronic infections, autoimmune diseases, allergies and transplantation-related complications, such as graft rejection or graft-versus-host disease (GvHD) (For a review, see Roncarolo, M. G. & Battaglia, M., *Nat Rev Immunol* 7, 585-98 (2007)).

Treg cells constitute of about 2-10% of CD4+ T cells in humans and rodents and constitutively express CD25, CTLA-4 and GITR, as well as the transcription factor Foxp3, which is involved in their development and function. The characteristic marker of Treg cells is Foxp3. Methods for the isolation of human Foxp3+ Treg cells are known. For instance, Hoffmann, P. et al. *Biol Blood Marrow Transplant* 12, 267-74 (2006) describe the isolation of CD4+CD25+ T cells with regulatory function from standard leukapheresis products by using a 2-step magnetic cell-separation protocol under good manufacturing practice (GMP) conditions. The generated cell products contained on average 49.5% Foxp3+ Treg cells. Also, commercial kits, e.g. CD4+CD25+ Regulatory T Cell Isolation Kit from Miltenyi Biotec or DYNAL® CD4+CD25+ Treg Kit from Invitrogen are available.

All of the hitherto described methods for isolation of human Foxp3+ Treg cells employ positive selection of Foxp3+ Treg cells based on cell surface markers of Tregs (see, e.g. Seddiki, N. et al., *J Exp Med* 203, 1693-700 (2006)). That is, the Foxp3+ Treg cells are isolated by using antibodies for Treg associated cell surface markers, mostly CD25. Yet most cell surface markers of Tregs, such as CD4 and CD25, are not restricted to Tregs. For instance, the commonly employed CD25 is not present on all Foxp3+ Treg cells and is also expressed by effector and memory CD4+ T cells (see, e.g. Baecher-Allan, C., Brown, J. A., Freeman, G. J. & Hafler, D. A., *J Immunol* 167; 1245-53 (2001)). Consequently, these positive selection methods do not permit the isolation of a uniform population that accounts for most of the Foxp3+ Treg cells as outlined above; Hoffmann, P. et al. obtained on average 49.5% Foxp3+ Treg cells.

Another disadvantage of current methods is the contamination of the isolated Treg subsets with effector T cells. The latter represent an inherent risk of adverse reactions as they drive pro-inflammatory immune reactions by secreting cytokines such as IFN-γ or IL-17. When employing markers such as CD25 these contaminations can be significant as up to half of the isolated CD4+ cell population can be comprised of effector T cells (Hoffmann, P. et al. *Biol Blood Marrow Transplant* 12, 267-74 (2006)).

Also, application of Foxp3+ Treg cells that have been isolated by positive selection based on cell surface markers of Tregs, in cellular therapy poses severe problems. First, isolation of Foxp3+ Treg cells based on cell surface markers, e.g. CD25, leads to more or less severe contaminations of the Foxp3+ Treg cell population with other cells, e.g. CD4+ effector cells which represent the main target of Treg suppression. Accordingly, there is a high risk if such positively selected Foxp3+ Treg cells were to be applied in cellular therapy as it might lead to a potentially fatal activation of the immune system of the patient treated. Such a fatal immune response was recently documented in the failure of the 'Tegenero' trials, where an antibody expected to expand Treg cells led to an activation of effector cells (Suntharalingam, G. et al., *N Engl J Med* 355, 1018-28 (2006)). Second, positively selected Foxp3+ Treg cells which have been tagged by an antibody may exhibit impaired function. For instance, cells tagged by an antibody are potentially preactivated, may suffer complementor cell-mediated depletion or exhibit altered homing and migration patterns. Accordingly, Foxp3+ Treg cells targeted by antibodies during their isolation are undesirable for a therapeutic use not only for safety reasons.

As discussed, the methods and kits described above show major disadvantages with respect to isolating Foxp3+ Treg cells. Firstly, the current methods for the isolation of immune-suppressive Foxp3+ Treg cells do not allow an effective removal of contaminating CD4+ effector and memory T cells. This is because the currently employed techniques and markers, e.g. CD25-based Foxp3+ Treg isolations, fail to discriminate these contaminating CD4+ effector and memory T cells from immune-suppressive Foxp3+ Treg cells. For instance, CD25 is a marker that is also present on these contaminating CD4+ cells. Moreover, at least some of these contaminating CD4+ cells cannot even be discriminated by intracellular Foxp3 staining, since activated human CD4+ effector cells are known to express Foxp3 transiently (Allan et al., *Int Immunol.* 19:345-54(2007)). As a result, even highly pure populations of $CD25^{high}CD4+$ T cells isolated by current methods contain a substantial fraction of cytokine producing pro-inflammatory effector cells (Dieckmann et al., *J. Exp Med.* 193, 1303-1310 (2001)), i.e. the isolated Foxp3+ Treg cells are significantly contaminated with CD4+ effector and memory T cells.

Additionally, so far no method exists that allows access to Foxp3+ Treg cells by negative selection, i.e. leaving the Foxp3+ Treg cells label/antibody-free.

From the foregoing it follows that there is a particular need for methods and kits/compositions useful for isolating Foxp3+ Treg cells which are virtually free from CD4+ effector and memory T cells. There is also a particular need for methods that do not require positive selection of Foxp3+ Treg cells.

SUMMARY OF THE INVENTION

It is therefore an object of the present invention to provide a method which avoids the above mentioned disadvantages of the prior art. In particular, it is an object of the present invention to provide a method for the isolation of immune-suppressive Foxp3+ Treg cells allowing the effective removal of cytokine producing CD4+ cells including transiently Foxp3 expressing CD4+ effector cells, which contaminate current CD25-based Treg preparations. Additionally, it is a further object of the present invention to provide a kit for the isolation of Foxp3+ Treg cells. Also, by introducing a novel marker that allows for the discrimination of cytokine-producing effector T cells from Foxp3+ Treg cells, the method and kit of the present invention offer a new approach to improve the quality of Treg preparations over those obtained by other methods, especially due to the removal of cytokine-producing effector T cells.

BRIEF DESCRIPTION OF THE DRAWINGS

FIG. 8: Removal of cytokine producing effector cells from CD127− Treg preparations. The experiment was carried out as in FIG. 2a except that purified CD4+ T cell subset were stimulated after the sorting with PMA/ionomycin to measure the cytokine production. The FACS analysis was carried out as in FIG. 2a except that the cells were stained intracellular with α-IFN-γ and α-1L-17.

DETAILED DESCRIPTION OF THE INVENTION

Figure 1:
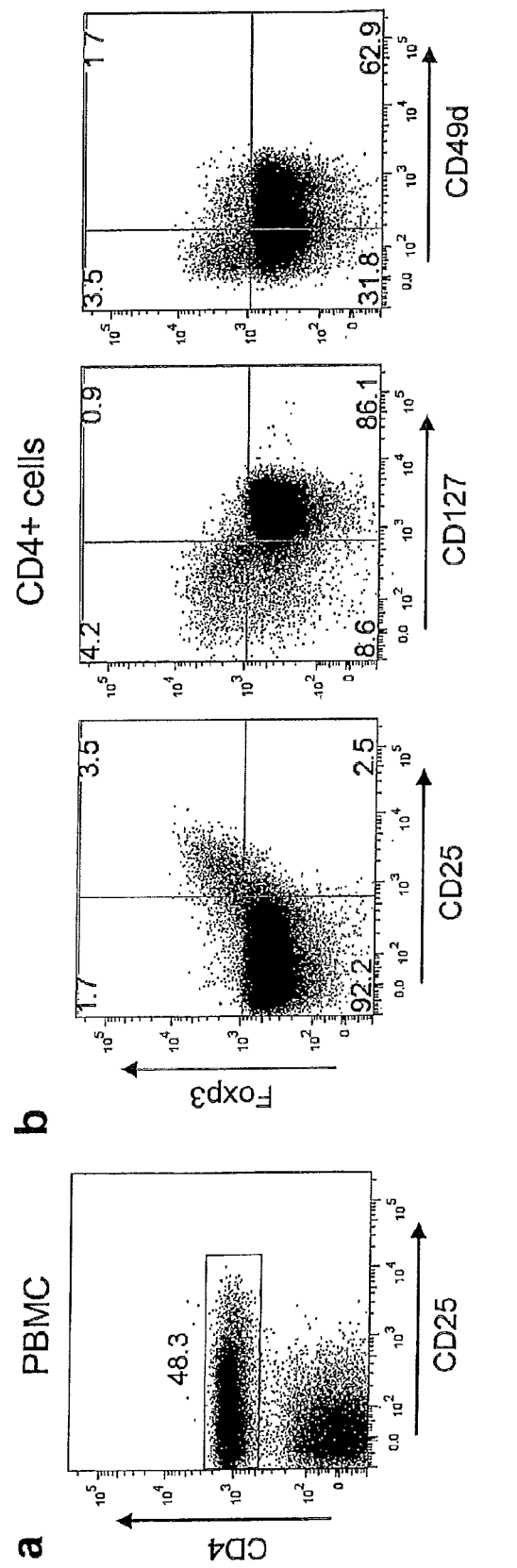
FIG. 1: Inverse correlation of CD127 and CD49d with Foxp3 expression. Human PBMC were stained for CD4, CD25, CD127, CD49d and Foxp3 and analyzed by FACS. a. Double staining of human PBMC for CD4 and CD25. Percentage of CD4+ cells of total PBMC is indicated. b. Correlation of CD25, CD127 and CD49d with Foxp3 expression. Human PBMC were stained for CD4, CD25, CD127, CD49d and Foxp3 and analyzed by FACS. Co-staining of Foxp3 with CD25 (left panel), CD127 (middle panel) and CD49d is shown for CD4+ cells gated according to FIG. 1a. Numbers indicate percentage of cells in each quadrant.

The present invention is based on results about the correlation of specific cell surface markers of Foxp3+ Treg cells and cell surface markers of non-regulatory CD4+ T cells. In particular, the cell surface marker CD49d was examined. During the experiments in the context of the present invention, it could be shown that the surface marker CD49d is absent in most Foxp3+ Treg cells. In the context of the present invention, it could be shown that human Foxp3+ Treg cells can be isolated by the use of an antibody against CD49d. Additionally, the suppressor activity of the isolated Foxp3+ Treg cells was confirmed by experiments in the context of the present invention. The isolated Foxp3+ Treg cells were able to suppress effector T cell proliferation in a suppression assay, strongly inhibited mixed lymphocyte reactions (MLR) in vitro and prevented the fatal attack of transferred human PBMC in vivo in a GvHD model based on Rag2$^{-/-}$γc$^{-/-}$ mice.

In a first aspect of the present invention, one of its objects is solved by a method for isolating human Foxp3+ Treg cells from a sample containing (i) peripheral blood mononuclear cells, or 'PBMCs', (ii) a lymphocyte containing fluid, or (iii) a lymphocyte containing tissue, the method comprising the steps of:
 (a) treating the sample with an anti-CD49d antibody;
 (b) separating Foxp3+' Treg cells.

The term "treating the sample" as used in the present invention shall especially imply that the cells contained in the sample are brought into direct physical contact with the antibodies in a way that the antibodies can interact with the targeted cells. In other words, in the method according to the present invention the peripheral blood mononuclear cells (PBMCs), the lymphocyte containing fluid, or the lymphocyte containing tissue are contacted with an anti-CD49d antibody and Foxp3+ Treg cells are separated.

The term "separating" as used in the present invention refers to the removal by physical means either of one cell type, e.g. Foxp3+ Treg cells, from other cell types, e.g. CD4+ effector cells, or of all non-regulatory CD4+ T cells from Foxp3+ Treg cells, thereby retaining an enriched population of Foxp3+ Treg cells. It is also to be noted that the separation can be carried out in one step or in more steps, which steps can also be performed consecutively, i.e. a first separation can be carried out after a first treatment of the sample with one or more antibody/antibodies and then another treatment of the sample isolated from the first separation with one or more antibody/antibodies can be carried out followed by another separation, and so on. For a more detailed description of separation techniques it is referred to P. T. Sharpe, Methods of Cell Separation, Laboratory Techniques in Biochemistry and Molecular Biology, Vol. 18, ELSEVIER (1988), and D. Fisher, G. E., Francis, D. Rickwood (Eds.), Cell Separation: A Practical Approach, Oxford University Press (1999).

The term "sample" as used in the present invention refers to a body fluid or tissue that contains peripheral blood mononuclear cells, or 'PBMCs', or lymphocytes.

The term "lymphocyte containing fluid" as used in the present invention refers to any fluid that contains lymphocytes, such as synovial fluid. The term "lymphocyte containing tissue" as used in the present invention refers to any tissue that contains lymphocytes, such as spleen, thymus, lymph nodes, bone marrow, Peyer's patches, and tonsils.

As has been outlined above and in other terms, the invention solves the recited technical problem by a simple, highly reliable and reproducible method for the isolation of Foxp3+ Treg cells. In particular, as mentioned above, prior art methods rely on cell surface markers of Foxp3+ Treg cells, e.g. CD25. However, as explained, said methods only allowed the isolation of Foxp3+ Treg cells that were significantly 'contaminated with CD4+ effector and memory T cells. Moreover, as all of the current methods are CD25− based, all isolated Foxp3+ Treg cells are labelled, namely tagged by an antibody against one of the cell surface markers of the Foxp3+ Treg cells. Furthermore, said methods required at least two isolation steps: (i) depletion of non-CD4 cells; (ii) isolation of CD25+ cells by positive sorting. In contrast to this, the method of the present invention first of all allows the isolation of Foxp3+ Treg in a single step. This is, because the method of the present invention utilizes CD49d as marker that allows for the discrimination between effector T cells and Foxp3+ Treg cells. CD49d is present on the majority of CD4+ effector and memory T cells but absent on immune-suppressive Foxp3+ Treg cells. Accordingly, it can be employed to remove contaminating cells, e.g. cytokine-producing effector T cells, from Foxp3+ Treg preparations. The depletion of CD49d+ cells removes virtually all cytokine producing CD4+ cells, including transiently Foxp3 expressing effector cells, including transiently Foxp3 expressing effector cells, which contaminate CD25-based Treg preparations. This applies for total CD4+ cells and, most strikingly, for conventional preparations of CD25+ cells.

Thus, isolation of Foxp3+ Treg cells using the method according to the present invention is faster, easier and above all more effective with regard to the isolation of a uniform population that accounts for most of the Foxp3+ Treg cells contained in the sample. In other words, isolation of Foxp3+ Treg cells employing the method of the present invention yields a population of immune-suppressive Foxp3+ Treg cells that is virtually free from contaminating CD4+ effector and memory T cells. Finally, the method of the present invention can be automated, therefore further augmenting easy applicability of the method.

Preferably, the method for isolating Foxp3+ Treg cells according to the invention comprises: (a) treating a sample containing Foxp3+ Treg cells with an anti-CD49d antibody; and (b) depleting the sample of CD49d+ cells via the anti-CD49d antibody thereby isolating Foxp3+ regulatory T cells, wherein the sample is (i) peripheral blood mononuclear cells, or 'PBMCs', (ii) a lymphocyte containing fluid, or (iii) a lymphocyte containing tissue.

The most encouraging result obtained in accordance with the present invention was the finding that also untouched Foxp3+ Treg cells can be obtained with high purity, i.e. virtually free from contaminating CD4+ effector and memory T cells, by the combined, i.e. sequential or simultaneous, use of anti-CD49d antibody and anti-CD127 antibody, which target two cell surface markers, namely CD127 and CD49d, inversely correlated with Foxp3 expression, in the method according to the present invention. The isolated Foxp3+ Treg cells obtained by the method according to the present invention are fully functional, demonstrated by their capacity to inhibit mixed lymphocyte reactions in vitro and to prevent lethal xeno-GvHD responses in vivo. So far, contamination of isolated Foxp3+ Treg cells with non-regulatory CD4+ cells, e.g. effector and memory CD4+ cells, was the major drawback in isolation methods for Foxp3+ Treg cells. A considerable amount of non-regulatory CD4+ cells is present in Foxp3+ Treg cell populations isolated by positive selection based on cell surface markers of Tregs. For example, in the Foxp3+ Treg cell populations isolated under GMP conditions by Hoffmann, P. et al. *Biol Blood Marrow Transplant* 12, 267-74 (2006) using positive selection, on average more than 50% of the cells in these populations were non-regulatory CD4+ cells. Naturally, such considerable amounts of undesired non-regulatory CD4+ cells hamper the use of such Foxp3+ Treg cell populations, for example, in immunotherapy as mentioned above.

Preferably, in the method of the present invention steps (a) and (b) can be carried out simultaneously. Additionally, steps (a) and (b) can also be carried out repeatedly, i.e. a first step (a) and a first step (b) are carried out, followed by a second step (a) and a second step (b), optionally followed by a third, fourth, etc. step (a) and (b), respectively. Notably, if step (a) and (b) are carried out repeatedly, the respective sample of each subsequent step (i.e. second step (a) or (b), third step (a) or (b), etc.) is treated and separated individually and independently of any other sample. Thus, for example, if the sample is treated with anti-CD49d in a first step (a), followed by a first separation step (b) for Foxp3+ Treg cells, e.g. by using a commonly known separation method selected from centrifugation, cell elutriation, magnetic separation, fluorescence activated cell sorting, immunological separation, adhesion, complement lysis, or fluorescence activated cell sorting, than these Foxp3+ Treg cells of the first step (b) can be treated with, e.g. anti-CD25 antibody and/or anti-CD127 antibody, in a second step (a), followed by a second separation step (b), e.g. using magnetic cell separation, for the isolation of CD25+Foxp3+ Treg cells.

The advantage of carrying out steps (a) and (b) simultaneously lies in that the isolation of Foxp3+ Treg cells is less laborious, simple, fast and also more cost effective. The advantage of carrying out steps (a) and (b) repeatedly lies in that different cell markers, e.g. positive markers, such as CD4, CD25, or negative markers, such as CD127, can be used for the separation and cells carrying these particular markers can be isolated or removed in subsequent separation steps. Thus, a unique cell population having specific properties, e.g. particular cell surface receptors, can be isolated.

In the method according to the present invention step (a) can additionally comprise treatment of the sample with an anti-CD25 antibody. Preferably, Foxp3+ Treg cells that have been isolated using anti-CD49d antibody are treated with an anti-CD25 antibody followed by a separation of CD25+Foxp3+ Treg cells.

Preferably, the method for isolating Foxp3+ Treg cells according to the invention comprises: (a) treating a sample containing Foxp3+ Treg cells with an anti-CD49d and an antiCD25 antibody; and (b) depleting the sample of CD49d+ cells via the anti-CD49d antibody thereby isolating Foxp3+ regulatory T cells, wherein the sample is (i) peripheral blood mononuclear cells, or 'PBMCs', (ii) a lymphocyte containing fluid, or (iii) a lymphocyte containing tissue. Optionally, step (b) can additionally comprise positive selection of CD25+ cells via the anti-CD25 antibody.

The term "positive selection" as used in the present invention means that desired cells are removed from the repertoire of cells by labelling/capturing said desired cells, while leaving unwanted cells (label-)free.

Further, in the method according to the present invention step (a) can additionally comprise treatment of the sample with an anti-CD127 antibody.

Preferably, the method for isolating Foxp3+ Treg cells according to the invention comprises: (a) treating a sample containing Foxp3+ Treg cells with an anti-CD49d and an anti-CD127 antibody; and (b) depleting the sample of CD49d+CD127+ cells via the anti-CD49d antibody or the anti-CD127 antibody thereby isolating Foxp3+ regulatory T cells, wherein the sample is (i) peripheral blood mononuclear cells, or 'PBMCs', (ii) a lymphocyte containing fluid, or (iii) a lymphocyte containing tissue.

Further, in the method according to the present invention, step (a) can additionally comprise separation of non-CD4+ T cells from the sample.

The advantage of additionally separating non-CD4+ T cells from the sample lies in that non-CD4+ T cells are removed with higher efficiency and, as a result, the purity of the obtained cell population is higher.

In the method according to the present invention, non-CD4+ T cells can be separated from the sample by positive selection using an anti-CD4 antibody.

Further, in the method according to the present invention, one or more antibody/antibodies that allow for the specific depletion of non-CD4+ T cells from the sample can be used for the separation of non-CD4+ T cells by negative selection from the sample.

The term "negative selection" as used in the present invention means that unwanted cells are removed from the repertoire of cells by labelling/capturing said unwanted cells, while leaving the cells of interest (label-)free.

The advantage of separating non-CD4+ T cells from the sample by depletion lies in that CD4+ T cells remain clean and untouched.

Preferred according to the present invention is a method, wherein the antibody/antibodies used for the specific depletion of non-CD4+ T cells from the sample can be selected from the group comprising anti-CD8 antibody, anti-CD10 antibody, anti-CD14 antibody, anti-CD15 antibody, anti-CD16 antibody, anti-CD19 antibody, anti-CD35 antibody, anti-CD36 antibody, anti-CD49b antibody, anti-CD56 antibody, anti-CD66a antibody, anti-CD66b antibody, anti-CD66c antibody, anti-CD66d antibody, anti-CD89 antibody, anti-CDw92 antibody, anti-CD93 antibody, anti-CD111 antibody, anti-CD112 antibody, anti-CD123 antibody, anti-CD141 antibody, anti-CD156a antibody, anti-CD170 antibody, anti-TCRg/d antibody, anti-CD235a antibody, anti-CD282 antibody, and anti-CDw329 antibody, anti-β7-Integrin antibody or mixtures.

Preferred according to the present invention, anti-CD14 antibody, anti-CD15 antibody, anti-CD16 antibody, and/or anti-CD66b antibody can be used for the specific depletion of non-CD4+ T cells from the sample.

The advantage of using one or more antibody/antibodies selected from anti-CD14 antibody, anti-CD15 antibody, antiCD16 antibody, and anti-CD66b antibody for the specific depletion of non-CD4+ T cells is that this subset of antibodies is small compared to some commercially available subsets.

Further preferred according to the present invention's method, anti-CD14 antibody and/or anti-CD16 antibody and/or anti-CD66b antibody can be used for the specific depletion of non-CD4+ T cells from the sample.

Preferred according to the present invention is further a method, wherein at least one of the antibodies used in step (a) is labelled or immobilized.

The term "labeled" as used in the present invention means that a molecule, e.g. an antibody, is conjugated to a label.

Many different labels that can be conjugated to an antibody are known to the skilled artisan. For example, radioisotopes, e.g., $^{32}$p, $^{35}$S or $^{3}$H; fluorescence or luminescence markers, e.g. fluorescein (FITC), rhodamine, TEXAS RED, phycoerythrin (PE), allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA); antibodies or antibody fragments, e.g. F(ab)2 fragment; affinity labels, e.g. biotin, avidin, agarose, bone morphogenetic protein (BMP), matrix bound, haptens; and enzymes or enzyme substrates, e.g. alkaline phosphatase (AP) and horseradish peroxidase (HRP).

The term "immobilized" as used in the present invention refers to any support to which an antibody can be linked to, while retaining its activity. Preferably, the support may be the surface of a matrix, e.g. a nylon matrix; a microtiter plate or a similar solid plastic support; beads, e.g. agarose or magnetic, beads. Immobilized antibodies are for example described in U.S. Pat. No. 4,615,985 and in references cited therein.

The advantage of using labelled or immobilized antibodies compared to unlabelled antibodies is that labelled or immobilized antibodies can be easier used with standard equipment and also an adaptation to standard isolation techniques is facilitated.

Preferred according to the present invention, at least one antibody used in step (a) is immobilized.

Preferably, in the present invention is method, at least one antibody used in step (a) is immobilized on a nylon matrix.

The advantage of immobilizing an antibody on a nylon matrix lies is that immobilization on nylon matrices is very efficient and allows a flexible, easy, fast, simple and inexpensive column-based isolation of cells, Immobilization on a nylon matrix is, for example, described in U.S. Pat. No. 4,615, 985.

Further preferred according to the present invention's method, the antibodies used in step (a) can be uniformly labelled.

The advantage of uniformly labelling the antibodies lies in that the antibodies can be detected all at once.

Preferably, in the present invention's method, the label can be selected from the group comprising isotopes, fluorescence or luminescence markers, antibodies or antibody fragments, affinity labels, and enzymes or enzyme substrates.

Preferred according to the present invention's method, the anti-CD25 antibody can be labelled with biotin, fluorescein (FITC) or phycoerythrin (PE).

Preferred according to the present invention's method, the anti-CD127 antibody can be labelled with biotin, fluorescein (FITC) or phycoerythrin (PE).

Preferred according to the present invention's method, the anti-CD49d antibody can be labelled with biotin, fluorescein (FITC) or phycoerythrin (PE).

Preferred according to the present invention's method, step (b) can be carried out using centrifugation, particularly, density gradient centrifugation, cell elutriation, magnetic separation, fluorescence activated cell sorting, immunological separation, adhesion, complement lysis or flow cytometry.

Preferred according to the present invention's method, step (b) can be carried out using magnetic cell separation, fluorescence activated cell sorting, or a column-based immunological separation.

The term "column-based immunological separation" refers to a way of sorting cells, where antibodies employed in the method according to the invention can be attached to resins of chromatography columns and used to bind a cell that possesses an antigen recognized by the specific antibody.

Preferred according to the present invention's method, an anti-CD45RO antibody can be used as an additional antibody in step (a), and the isolated Foxp3+ Treg cells are CD45RA+ T cells.

The advantage of using an anti-CD45RO antibody as an additional antibody in step (a) lies in that a specific subset of Foxp3+ Treg cells, namely CD45RA+ T cells can be isolated in a highly efficient manner and a very-high purity.

Preferred according to the present invention's method, an anti-CD45RA antibody can be used as an additional antibody in step (a), and the isolated Foxp3+ Treg cells are CD45RO+ T cells.

The advantage of using an anti-CD45RA antibody as an additional antibody in step (a) lies in that a specific subset of Foxp3+ Treg cells, namely CD45RO+ T cells can be isolated in a highly efficient manner and a very high purity.

In a second aspect of the present invention, one of its objects is solved by a kit for isolating human Foxp3+ Treg cells, comprising an anti-CD49d antibody and an anti-CD25 antibody or an anti-CD49d antibody and an anti-CD127 antibody.

Further, the kit according to the present invention can comprise an anti-CD49d antibody, anti-CD25 antibody and an anti-CD127 antibody.

Preferably, the kit according to the present invention can additionally comprise one or more antibody/antibodies selected from the group comprising anti-CD8 antibody, anti-CD10 antibody, anti-CD14 antibody, anti-CD15 antibody, anti-CD16 antibody, anti-CD19 antibody, anti-CD35 antibody, anti-CD36 antibody, anti-CD49b antibody, anti-CD56 antibody, anti-CD66a antibody, anti-CD66b antibody, anti-CD66c antibody, anti-CD66d antibody, anti-CD89 antibody, anti-CDw92 antibody, anti-CD93 antibody, anti-CD111 antibody, anti-CD112 antibody, anti-CD123 antibody, anti-CD141 antibody, anti-CD156a antibody, anti-CD170 antibody, anti-TCRg/d antibody, anti-CD235a antibody, anti-CD282 antibody, and anti-CDw329 antibody, anti-β7-Integrin antibody or mixtures.

Further, the kit of the present invention can contain at least one antibody that is immobilized.

Moreover, the kit according to the invention can contain at least one antibody that is labelled.

Preferably, the kit of the present invention can contain antibodies that are uniformly labelled.

Preferred the kit according to the invention can contain labelled antibodies, wherein the label can be selected from the group comprising isotopes, fluorescence or luminescence markers, antibodies or antibody fragments, affinity labels, and enzymes or enzyme substrates.

Preferably, the kit can contain an anti-CD127 antibody, an anti-CD25 antibody, and/or an anti-CD49d antibody which can be labelled with biotin, FITC, or PE.

In a third aspect of the present invention, one of its objects is solved by a use of (i) an anti-CD49d antibody, (ii) antiCD49d antibody in combination with anti-CD25 antibody and/or anti-CD127 antibody, or (iii) of a kit according to the invention for the isolation of human Foxp3+ Treg cells. In particular, an anti-CD49d antibody; an anti-CD49d antibody in combination with an anti-CD25 antibody and/or an anti-CD127 antibody; or a kit according to the invention can be used for the isolation of human Foxp3+ Treg cells from a sample containing (i) peripheral blood mononuclear cells (PBMCs), (ii) a lymphocyte containing fluid, or (iii) a lymphocyte containing tissue.

Preferably, the use according to the invention can be characterized in that separation of the human Foxp3+ Treg cells can be achieved by separating CD49d+ PBMCs including non-regulatory CD4+ T cells from Foxp3+ Treg cells via centrifugation, cell elutriation, magnetic separation, fluorescence activated cell sorting, immunological separation, adhesion, complement lysis or flow cytometry.

Further, the use according to the invention can be characterized in that depletion of non-CD4+ T cells from the sample can be carried out using at least one antibody selected from the group comprising anti-CD8 antibody, anti-CD10 antibody, anti-CD14 antibody, anti-CD15 antibody, anti-CD16 antibody, anti-CD19 antibody, anti-CD35 antibody, anti-CD36 antibody, anti-CD49b antibody, anti-CD56 antibody, anti-CD66a antibody, anti-CD66b antibody, anti-CD66c antibody, anti-CD66d antibody, anti-CD89 antibody, anti-CDw92 antibody, anti-CD93 antibody, anti-CD111 antibody, anti-CD112 antibody, anti-CD123 antibody, anti-CD141 antibody, anti-CD156a antibody, anti-CD170 antibody, anti-TCRg/d antibody, anti-CD235a antibody, anti-CD282 antibody, and anti-CDw329 antibody, anti-β7-Integrin antibody or mixtures.

The present invention shall now be described further in the following examples with respect to the attached figures without being limited thereto. For the purposes of the present invention, all references as cited herein are incorporated by reference in their entireties. Additionally, the present invention is based on scientific experiments which have been performed on biological specimen derived from volunteers. Volunteers have given their consent to use the specimen for the study which is disclosed in the present invention.

EXAMPLE 1

Particular Methods and Materials Used in the Examples

Antibodies and Reagents. Antibodies specific for CD4 (RPA-T4), CD25 (MA251), and CD127 (hIL-7R-M21) were purchased from BD Bioscience. Anti-IFN-γ was purchased from Miltenyi Biotech (45-15). Anti-CD49d (BU49) was obtained from ImmunoTools. α-CD3 (UCHT-1) was produced at the MDC. αFoxp3 (PCH101) and α-IL-17 (eBio64CAP17) were purchased from eBioscience, intracellular staining was carried out according to manufacturer's recommendation. CFDA was obtained from Molecular Probes, $^3$H-thymidine from GE Healthcare.

Flow Cytometry and Cell Preparation. Human PBMC were obtained from healthy volunteers. Mononuclear cells were isolated by FICOLL gradient centrifugation (GE Healthcare). FACS analysis was carried out on a FACSCALIBUR or LSR II instrument (BD Bioscience). Data were analyzed using FACSDIVA software (BD Bioscience), CELLQUEST (BD Bioscience) or FLOWJO software (Treestar).

Cytokine Detection. Cells were stimulated for 4-6 h with PMA and ionomycin in the presence of brefeldin A for the last 3-4 h. The cytokine secretion was determined by intracellular staining with α-IL-17 and α-IFN-γ using MACS- or FACS-sorted CD4+ T cell subsets. Cells were used either freshly or maintained overnight in RPMI, supplemented with 50 U/ml IL-2, before stimulation.

Treg Isolation. Magnetic cell sorting was carried out using the MACS system (Miltenyi Biotech), FACS sorting with the FACSARIA instrument (BD Bioscience). A) Treg enrichment by CD49d depletion: MACS sorted (hCD4-isolation kit II/Miltenyi Biotech) were incubated for 10' with α-CD49d–FITC at 4-8° C. After washing with MACS buffer for 10' at 4-8° C., cells were incubated for 15' with 10 µl α-FITC-magnetic beads (Miltenyi Biotech) per $10^7$ cells at 4-8° C. After washing with MACS buffer, cells were separated using a LD-column (Miltenyi Biotech). B) Untouched two-step MACS-procedure: untouched human CD4+ T cells were first isolated from PBMC using hCD4-isolation kit II (Miltenyi Biotech). In a second step the cells were incubated for 10' with α-CD49d–FITC and α-CD127-biotin at 4-8° C. After washing with MACS buffer for 10' at 4-8° C., cells were incubated for 15' with 10 µl α-FITC-and 20 µl α-biotin-magnetic beads (Miltenyi Biotech) per $10^7$ cells at 4-8° C. After washing with MACS buffer, cells were separated using a LD-column (Miltenyi Biotech). C) Untouched single-step MACS procedure: human PBMC were incubated with FITC-labelled α-CD49d, biotin-labelled α-CD127 and the biotin-labelled antibody-mix of the human CD4+ T cell isolation kit II for 10' at 4-8° C. After washing with MACS buffer, cells were incubated with 10 µl α-FITC- and 25 µl α-biotin magnetic-beads per $10^7$ cells for 15' at 4-8° C. After washing with MACS buffer, cells were separated using LD-column. D) Untouched single-step MACS procedure (CD49d and CD127 depletion only): human PBMC were incubated with FITC-labelled α-CD49d, biotin-labelled α-CD127 for 10' at 4-8° C. After washing with MACS buffer, cells were incubated with 15 µl α-FITC-and 20 µl α-biotin magnetic-beads per $10^7$ cells for 15' at 4-8° C. After washing with MACS buffer, cells were separated using a LD-column. E) FACS-sortings: untouched CD4+ T cells were obtained from human PBMC using the human CD4+ T cell isolation kit II (Miltenyi Biotech). Cells were stained with α-CD49d–FITC and α-CD127–PE for 10' at 4-8° C. After washing with MACS buffer, cells were resuspended in MACS buffer and sorted on the cell sorter. Untouched Treg cells were obtained using a sorting gate for CD49d−CD127− cells. For FACS-sortings of CD25+ cells, human PBMC were stained with α-CD49d, α-CD4 and α-CD25 for 10' at 4-8° C. After washing with MACS buffer, cells were resuspended in MACS buffer and sorted on the cell sorter using a sorting gate for CD4+CD25$^{high}$CD49d+ or CD4+CD25$^{high}$CD49d− cells. Dead cells were excluded by propidium iodide (Sigma).

CFDA-Based Proliferation Assay. CD4+ effector cells were labelled with 0.5 µM 5-carboxyfluorescein diacetate (CFDA; Molecular Probes) as described before (Kleinewietfeld, M. et al. *Blood* 105, 2877-86 (2005)). CD4+ effector T cells (25,000 cells/well) were incubated with irradiated CD4-depleted PBMC (50,000 cells/well; 3000 rad) and 10 µg/ml anti-CD3 (UCHT-1) for 3-4 days in 96 well V-bottom plates (Costar). For T cell suppression Treg cells were added at the indicated ratio. Proliferation of CD4+ T cells was analyzed by FACS.

Mixed Lymphocyte Reaction (MLR). MLR with human PBMC was carried out as described (Ebert, L. M. & McColl, S. R. *J Immunol* 166, 4870-8 (2001)). Human PBMC (100,000 cells/well) were incubated with irradiated (3000 rad) allogeneic PBMC (100,000 cells/well) in RPMI/10% FCS (Invitrogen) for 5 days. For suppression of proliferation, isolated autologous Treg cells were added at the indicated ratio. Proliferation was monitored by $^3$H-thymidine incorporation (1 µCi/well) for additional 10-15 h of culture and determined using a beta-plate reader (Wallac).

Xenogeneic-Graft Versus Host Disease (x-GvHD). An acute form of GvHD was induced in Rag2$^{−/−}$γc$^{−/−}$ mice (purchased from Taconic) as described before[9]. In brief, PBMC were depleted with α-CD25 microbeads (Miltenyi Biotech) using a LD column (Miltenyi Biotech). Treg cells were obtained from PBMC of healthy donors using the one step procedure. One day before transfer, mice received i.v. 0.2 ml clodronate-containing liposomes. 4 h prior to the transfer of cells, mice were irradiated (350 rad). 30×10$^6$ CD25 depleted PBMC were injected i.v., either alone or as mixture with 0.5×10$^6$ Treg cells in PBS/0.1% human serum albumin. The weight of the mice and the clinical symptoms were determined over the entire period of the experiment; clinical signs of the disease were ruffled fur, hunched posture and impaired movement.

EXAMPLE 2

CD127 and CD49d are Inversely Correlated with Foxp3

Depending on the donor, about 30-60% of human PBMC are CD4+ T cells (FIG. 1a), of these, approximately 3-10% are Treg cells. While most human Treg cells express high levels of the IL-2 receptor α-chain CD25 (CD25$^{high}$), this marker does not separate the Treg population from non-regulatory CD4+ cells as clearly as in mice. Also some effector and memory CD4+ cells express lower amounts of CD25 (CD25$^{low}$), so that their population partly overlaps with the CD25$^{high}$ Treg subset (Baecher-Allan, C., Brown, J. A., Freeman, G. J. & Hafler, D. A., *J Immunol* 167, 1245-53 (2001)). Treg separations based on this marker therefore have an inherent risk of being contaminated by these cells. Like several other genes, CD25 expression on Treg cells is driven directly by Foxp3 (Hori, S., Nomura, T. & Sakaguchi, S., *Science* 299, 1057-61 (2003)). Counterstaining with Foxp3 therefore indicates a near linear correlation for the CD25$^{high}$ cells, in which cells expressing the highest amounts of Foxp3 also stain brightest for CD25 (FIG. 1b, left panel).

In contrast to CD25, the α-chain of the IL-7 receptor (CD127) is inversely correlated with Foxp3 expression (Liu, W. et al., *J Exp Med* 203, 1701-11 (2006); Seddiki, N. et al., *J Exp Med* 203, 1693-700 (2006)) (FIG. 1b, middle panel). Also here the correlation is nearly linear, but cells with highest level of Foxp3 have the lowest expression level of CD127. The segregation, however, is not complete. In the example shown in FIG. 1b (middle panel), about ⅔ of the CD127– cells were also Foxp3–. For the characterization of Treg cells CD127 is therefore always used in combination with CD25 (Liu, W. et al, *J Exp Med* 203, 1701-11 (2006); Seddiki, N. et al., *J Exp Med* 203, 1693-700 (2006)).

Our own studies have identified a second surface marker absent on most Treg cells. CD49d is the α-chain of the integrin VLA-4 ($α_4β_1$). Also here the co-segregation is incomplete (FIG. 1b, right panel). An inverse linear correlation with Foxp3, as observed for CD127, however, does apparently not exist. Double-staining instead revealed absence of CD49d in Foxp3+ cells independent of the level of Foxp3 expression.

EXAMPLE 3

CD49d Discriminates Foxp3+ Treg Cells from Foxp3–CD127– Cells

While the segregation of both markers with Treg cells was incomplete, the combined use of CD127 and CD49d may complement each other. Double-staining with α-CD127 and α-CD49d allowed dividing the population of CD4+ cells into the three major populations: CD127+, CD49d+CD127– and CD49d–CD127– cells (FIG. 2a, upper panel). Staining with α-CD25 and α-Foxp3 confirmed that the vast majority of the CD127+ cells were non-regulatory CD25–Foxp3– cells (FIG. 2a, lower left panel). More importantly, CD49d divided the CD127– subset into two nearly equally large subpopulations. The majority of CD49d+CD127– cells were Foxp3–, only less than 18% were CD25+Foxp3+ (FIG. 2a, lower right panel). The CD49d–CD127– population, in contrast, consisted almost exclusively of Foxp3+ cells. More than 83% of the cells were CD25+Foxp3+ Treg which express high levels of Foxp3 (FIG. 2a, lower middle panel).

To confirm that the CD49d–CD127– phenotype correlates with suppressive capacity, CD49d+CD127– and CD49d–CD127– cells were isolated by FACS sorting from CD4+ PBMC (FIG. 2b). Almost no inhibition was observed with the CD49d+CD127– subset (FIG. 2c). In contrast, CD4+ cells sorted only based on the absence of CD49d and CD127 effectively prevented the expansion of activated CD25–CD4+ cells. Thus, the use of CD49d allows discriminating the non-suppressive CD127– cells from functional Foxp3+ Treg cells.

EXAMPLE 4

Purification of Untouched Foxp3+ Treg Cells by MACS

Figure 3:
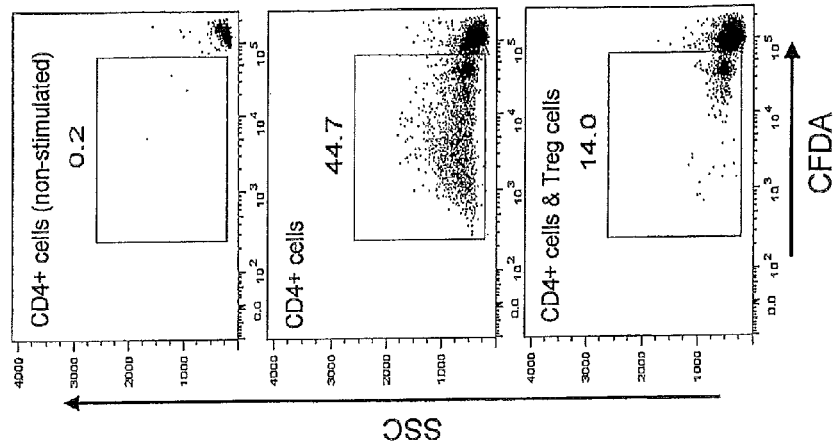
FIG. 3: Isolation of untouched Foxp3+ Treg cells from CD4+ T cells by MACS. Untouched CD4+ cells of human PBMC isolated by MACS with a commercial CD4 isolation kit were depleted by MACS in a second step of CD127/CD49d− expressing cells. a. FACS analysis of depleted cells. FACS plots are shown for the CD4+ cell population prior to the depletion (left panels) and for the cells remaining after CD49d/CD127 depletion (right panels). Data is shown for the staining CD49d vs. CD127 (upper panels) and CD25 vs. Foxp3 (lower panels). Percentage refers to the number of cells in each quadrant. b. Suppressive capacity. CD4+ T cells depleted of CD49d/CD127+ cells were used as suppressor cells (Treg) in a FACS-based in vitro assay. CD4+ effector cells removed by the depletion were labeled with CFDA and used as responder cells. The panels indicate the CFDA staining of CD4+ cells without any stimulation (upper panel), after incubation with α-CD3 (middle panel) or after incubation with α-CD3 in the presence of untouched Treg cells at a ratio of 1:1 (lower panel). Numbers represent the percentage of dividing CD4 effector cells.
Figure 3:
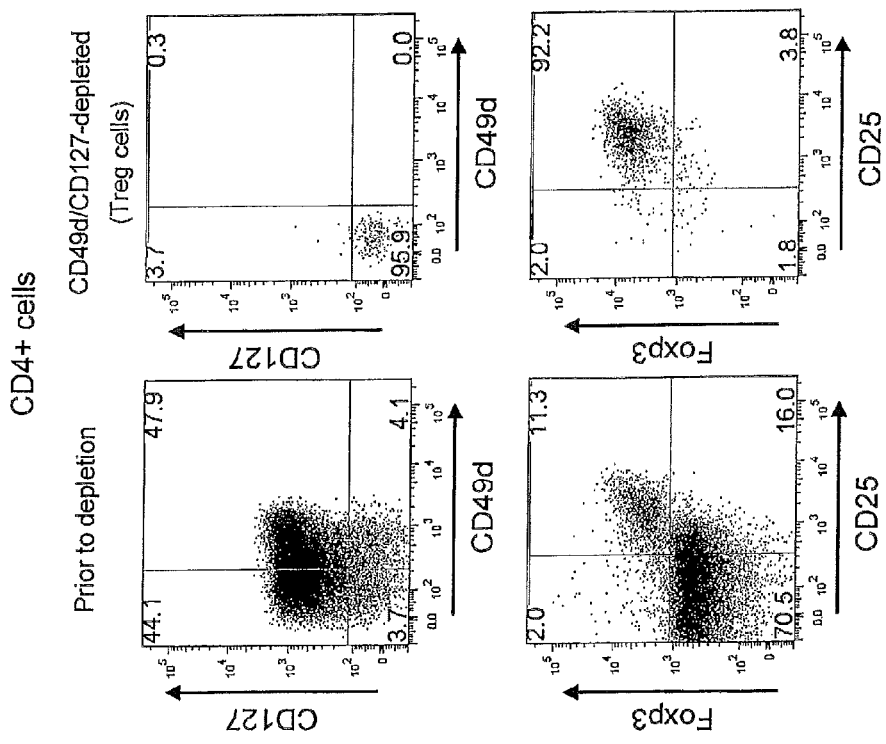

The result of the FACS sorting experiment indicated that the combined depletion of CD4+ T cells with α-CD127 and α-CD49d by MACS should produce a clean population of untouched Treg cells. To validate applicability of this approach, untouched CD4+ cells isolated before from human PBMC were labelled with α-CD127 and α-CD49d and depleted by MACS using conventional magnetic bead-labelled antibodies (FIG. 3). The analysis by FACS revealed that the depletion produced a population of CD49d–CD127– cells with a purity >95% (FIG. 3a, upper panel). Staining of CD25 and Foxp3 confirmed that more than 92% of these cells were CD25+Foxp+ cells, additional 2% were CD25Foxp3+ (FIG. 3a, lower panels). To confirm the functionality of the isolated Treg cells, the cells were tested in a FACS-based in vitro suppression assay (FIG. 3b). CD4+ effector cells were labelled with CFDA to monitor the proliferation. Without any stimulation the cells did not divide (FIG. 3b, upper panel), but stimulation with α-CD3 triggered a proliferative response indicated by the reduced CFDA fluorescence of about 45% of the cells (FIG. 3b, middle panel). The addition of MACS purified Treg cells inhibited the proliferation to 14%, which mostly stopped the expansion already after a single replication cycle (FIG. 3b, lower panel). Thus, untouched Treg cells isolated by MACS-depletion with α-CD127 and α-CD49d are fully able to suppress autologous CD4+ effector cells in vitro.

EXAMPLE 5

Purification of Untouched Foxp3+ Treg Cells from PBMC by MACS in a Single Step

Figure 4:
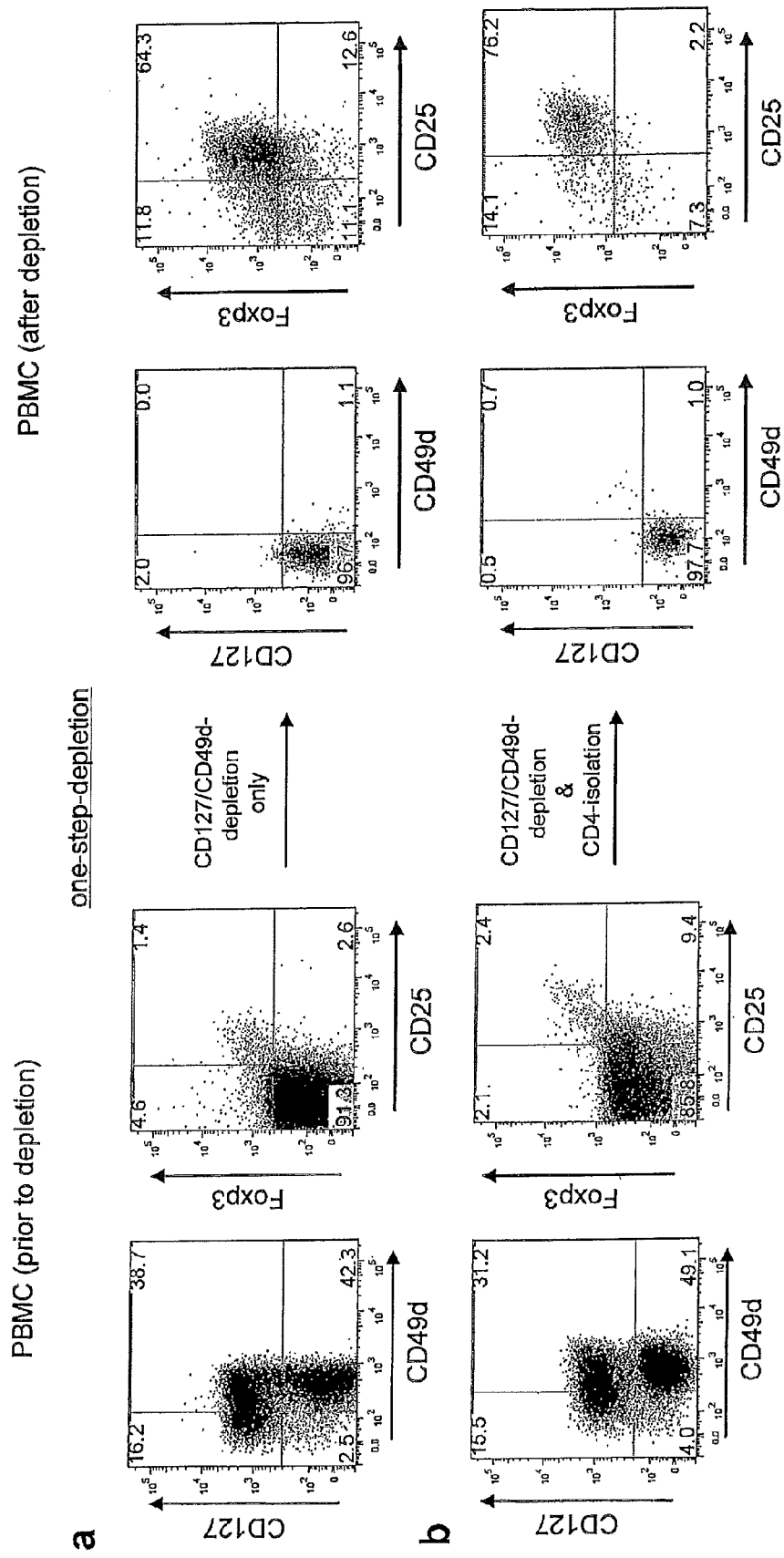
FIG. 4: Isolation of untouched Treg cells from PBMC. Treg cells were isolated by MACS-depletion from total PBMC. a. Depletion with α-CD49d/α-CD127 only. Depletion of human PBMC was carried out with α-CD49d and α-CD127 as described in FIG. 3 except that total PBMC instead of purified CD4+ cells were used. b. Single-step depletion with α-CD49d/α-CD127 in combination with a CD4+ T cell isolation kit. To increase the purity α-CD127 and α-CD49d was added to the antibody mix of a commercial CD4+ T cell isolation kit. The staining of CD49d vs. CD127 and of CD25 vs. Foxp3 is shown for PBMC prior to depletion (left panels) and for the bead-negative fraction obtained after the depletion (right panels). Numbers indicate the percentage of cells in each quadrant.

The selectivity of CD49d is particularly striking when using total PBMC instead of pre-purified CD4+ cells (FIG. 4). In contrast to CD127, which is absent on almost half of the PBMC, the vast majority of non-CD4+ T cells still expresses CD49d (FIG. 4, left panels). Within total PBMC 40-50% were CD49d+CD127–, leaving only about 2-4% of CD49d–CD127– cells. The depletion of CD49d+/CD127+ cells alone was therefore already sufficient to obtain untouched Foxp3+ cells directly from PBMC with a purity >75% (11.8% CD25–Foxp3+, 64.3% CD25+Foxp3+; FIG. 4a). The purity could be further increased when α-CD49d/α-CD127 was added to the antibody mixture of a commercial CD4+ T cell isolation kit (FIG. 4b). FACS-analysis of the PBMC fraction after depletion revealed here that >90% were Foxp3+ cells (76.2%

CD25+Foxp3+, 14.1% CD25−Foxp3+). The purity of the cells obtained by single-step PBMC depletion was therefore comparable to the purity obtained with previously isolated CD4+ T cells (compare FIG. 3).

EXAMPLE 6

Inhibition of Allo-/Xenogeneic Reactions in Vitro and In Vivo

Figure 5:
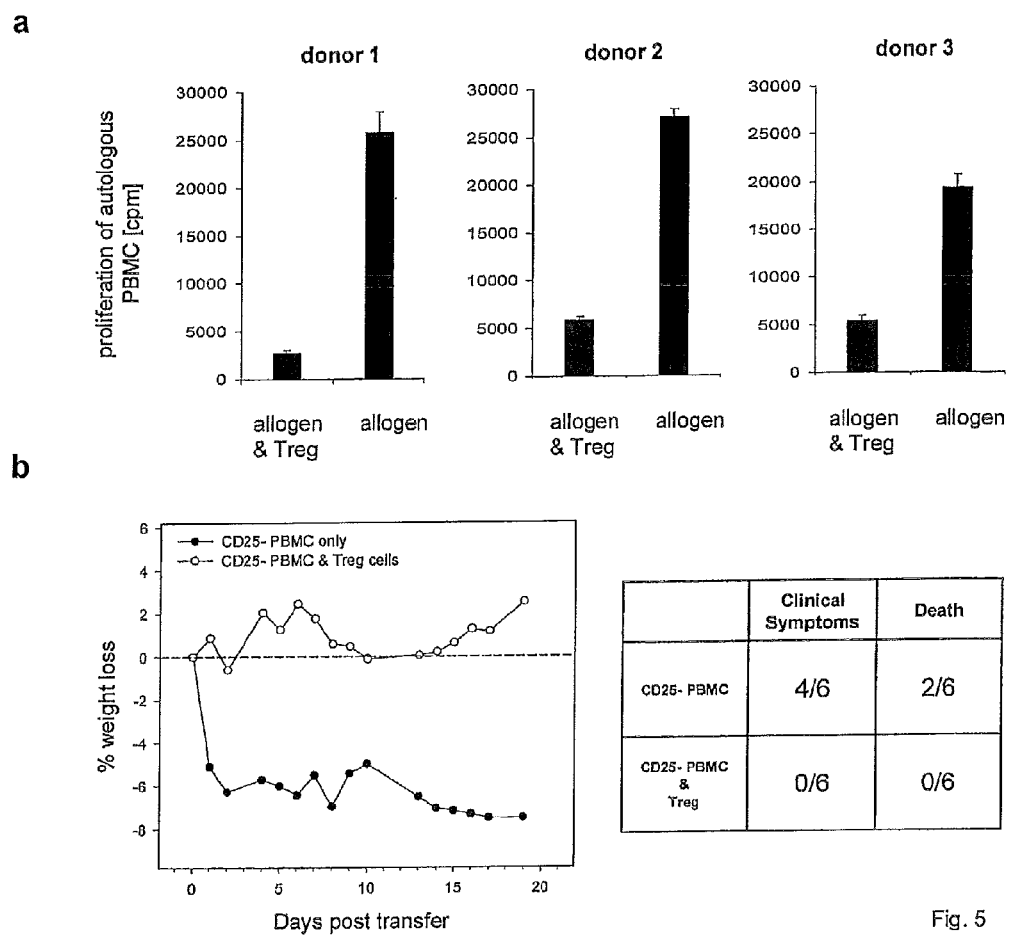
FIG. 5: Inhibition of mixed lymphocyte reaction (MLR) in vitro and prevention of GvHD in vivo. Untouched Treg cells were isolated from human PBMC by a single-step CD127/CD49d− depletion as described in FIG. 4. a. Inhibition of MLR. MLR reaction is shown for three different donors. In each reaction $10^5$ PBMC were incubated with the same number of radiated PBMC of a haplotype-mismatched second donor (allogen). The reaction was inhibited by adding 2.5× $10^4$ autologous Treg cells isolated in a single step MACS depletion (allogen & Treg). Proliferation was determined by $^3$H-thymidine incorporation and is expressed as 'counts per minute' (cpm). b. Prevention of acute GvHD. Acute xeno-GvHD was induced by the adoptive transfer of 30×$10^6$ CD25 depleted human PBMC (CD25− PBMC) into Rag2$^{-/-}$γc$^{-/-}$ mice. Progression of the disease was recorded by determining the weight loss (left panel). One group received only CD25− PBMC (filled circle), a second group received CD25− PBMC together with 0.5×$10^6$ untouched autologous Treg cells in a co-transfer (open circle). Groups of 6 mice were used; the average relative weight was determined in reference to the start of the experiment and is expressed as 'percent weight loss'. Incidence of clinical signs (ruffled fur, hunched posture and immobility) and death is indicated in the right panel.

To confirm function and viability of Treg cells isolated by direct PBMC-depletion, the suppressive capacity was tested in a mixed lymphocyte reaction (MLR). MLR is the in vitro correlate of GvHD. It is based on the allogeneic activation of T cells by 'foreign' MHC molecules, evident after mixing PBMC of two different donors. To determine whether the Treg cells are able to control the alloreactive response, they were added to non-radiated autologous PBMC mixed with radiated PBMC of haplotype-mismatched donors (FIG. 5a). In these experiments, Treg cells purified from PBMC according to Example 5 (FIG. 4b) proved to be potent suppressors of the allogeneic response. As shown for three different donors, the presence of Treg cells strongly suppressed the proliferation of autologous PBMC. Thus, untouched PBMC-derived Foxp3+ cells are fully functional Treg cells able to control allogeneic immune responses in vitro.

The MLR experiment clearly demonstrated the suppressive capacity of the isolated Treg cells in vitro. With regard to future therapeutic applications, it is crucial, however, to demonstrate that untouched Treg cells can also suppress destructive immune responses in vivo. For this purpose an acute GvHD in vivo model was used, which is based on the transfer of CD25-depleted human PBMC into $Rag2^{-/-}\gamma c^{-/-}$ mice (Mutis, T. et al., *Clin Cancer Res* 12, 5520-5 (2006)). The elimination of Treg cells from the transferred cell population allows simulating a particularly aggressive form of the disease which frequently leads to the death of the animals. Depletion of Treg cells from PBMC was carried out by MACS using α-CD25 microbeads, untouched Treg cells were isolated again in a single step by combined use of α-CD127/α-CD49d together with a commercial CD4+ isolation kit (according to Example 5, FIG. 4b). All mice that received $30\times10^6$ CD25-depleted PBMC exhibited a more or less pronounced weight loss within the first days of the experiment (FIG. 5b). Four of the six mice developed clinical symptoms and of these two mice died during the experiment. In line with a previous publication, the severity of PBMC-induced GvHD was diminished when autologous Treg cells were co-transferred (Mutis, T. et al., *Clin Cancer Res* 12, 5520-5 (2006)). In this case, $0.5\times10^6$ untouched Treg cells were sufficient to completely abrogate the weight loss and all mice of the treated group remained without symptoms for the entire course of the experiment. Thus, untouched Treg cells isolated by CD127/CD49d- depletion are potent suppressor cells capable to control destructive immune responses both in vitro and in vivo.

EXAMPLE 7

Separation of Contaminating Effector Cells from Treg Preparations

Figure 6:
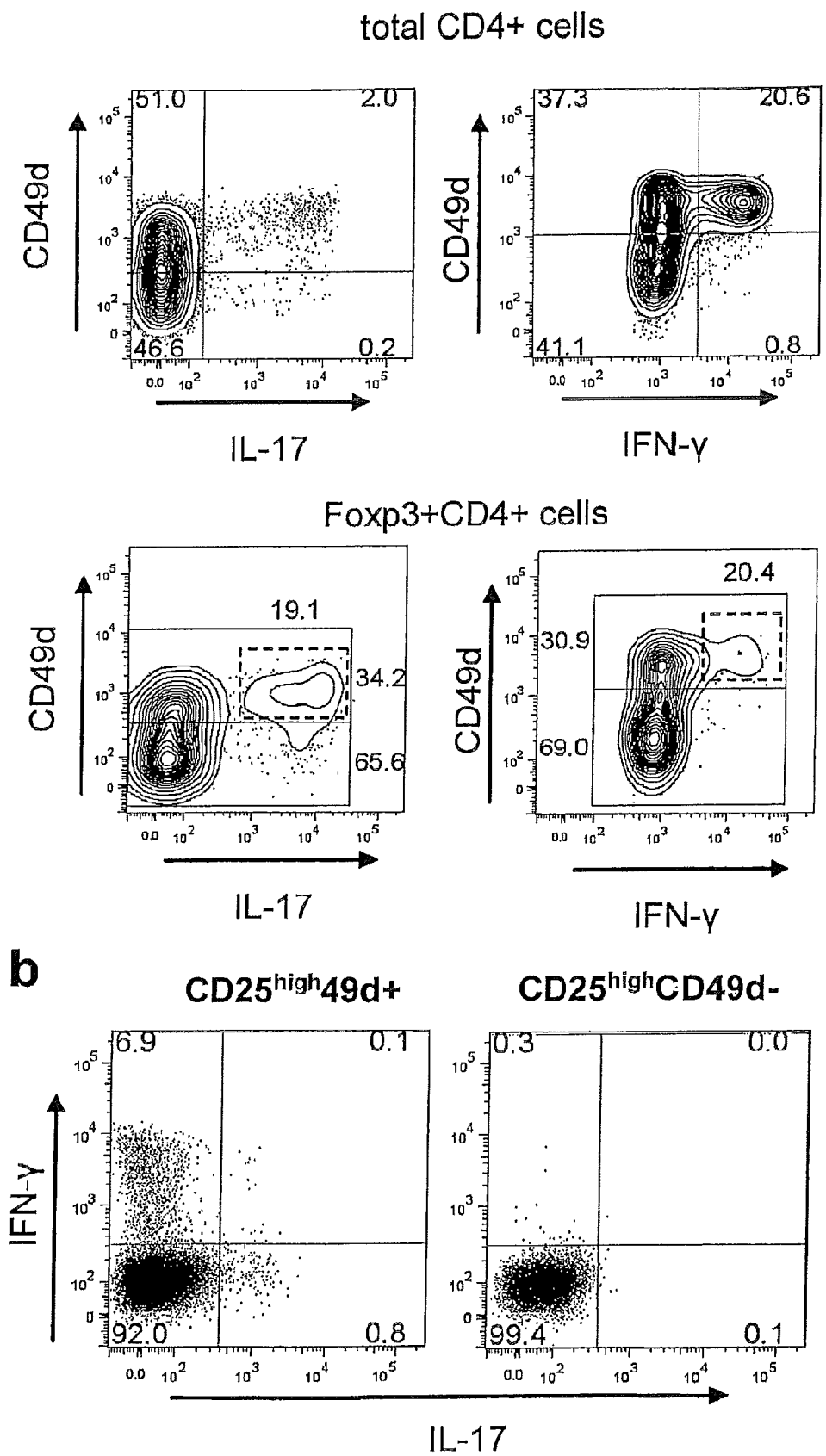
FIG. 6: Purification of CD25+ Treg cells by α-CD49d depletion. a. Segregation of CD49d expression with cytokine secretion. Cytokine secreting CD4+ cells express CD49d. CD4+ T cells were stimulated in vitro with PMA/ionomycin and analyzed 6 h later by FACS. Staining of total CD4+ cells (upper panels) and Foxp3+CD4+ cells (lower panels) is shown for CD49d vs. IL-17 (upper left panel) or for CD49d vs. IFN-γ (upper right panel). Percentages of total CD4+ cells refer to number of cells per quadrant. Percentages of Foxp3-gated CD4+ cells refer to the fraction of CD49d+ or CD49d− cells, percentage of cytokine secreting cells in the dashed gate are in reference to the number of CD49d+ cells. b. CD49d removes Th1- and Th17-like cells from CD25$^{high}$ Treg preparations. Human Treg cells are characterized by CD25$^{high}$ expression. PBMC were stained with α-CD4, α-CD25 and α-CD49d and sorted by FACS into the CD4+ subsets CD49d+CD25$^{high}$ and CD49d−CD25$^{high}$. The sorted cells subsets were activated with PMA/ionomycin and stained intracellular for IFN-γ and IL-17. Percentages represent the number of cells in the indicated quadrant.

CD25 is expressed in high amounts by Treg cells ($CD25^{high}$). In humans, however, the marker is expressed in lower amounts also by proinflammatory cells including effector and memory CD4+ T cells (Baecher-Allan et al., *J Immunol.* 167: 1245-53 (2001)) and activated CD4+ T cells transiently expressing Foxp3 (Allan et al., *Int. Immunol.* 19: 345-54 (2007)). In contrast to Treg cells, these effector cells are able to secrete proinflammatory cytokines such as IFN-γ or IL-17. As shown in FIG. 6a, CD49d expression segregates with the ability to secrete cytokines. This applies both for total CD4+ cells as well as for the subset of Foxp3+ cells. Hence, CD49d can be used to remove contaminating cytokine secreting effector cells from Treg preparations based on CD25-isolation. In case of FACS-sorting (FIG. 6b) pure Treg cells can be obtained by gating on the CD49d−$CD25^{high}$CD4+ subset, for MACS-sorting the cells will be depleted with α-CD49d prior to the sorting procedures involving positive isolation with α-CD25.

EXAMPLE 8

Depletion with CD49d Alone Leads to Treg Enriched CD4 Cell Preparations

Figure 7:
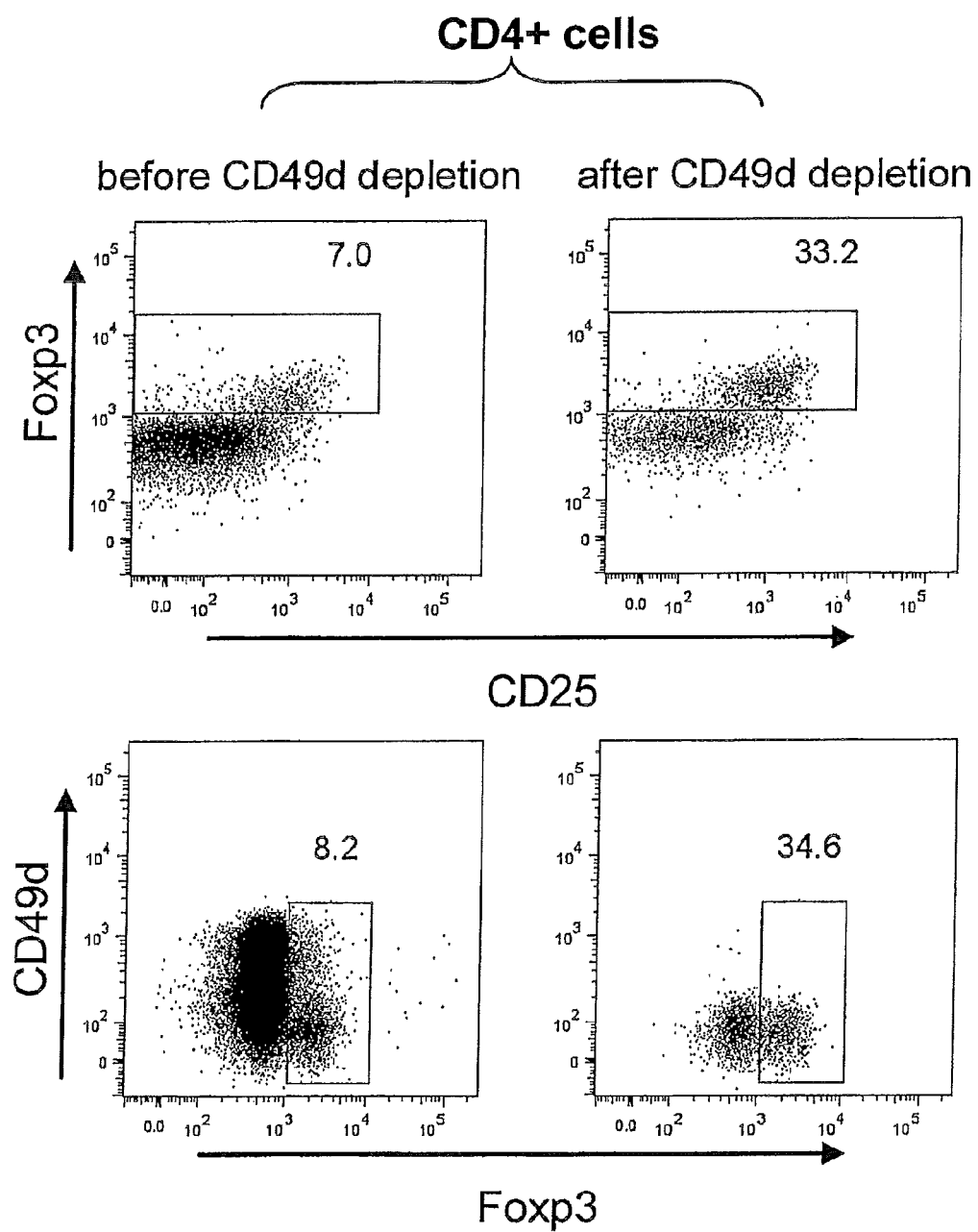
FIG. 7: Enrichment of Foxp3+ Treg by depletion of CD49d+ cells from human CD4+ T cells. Human CD4+ cells were depleted by CD49d and analyzed by FACS for CD25 and Foxp3 expression. Left panels: Total CD4+ cells, right panels: CD49d depleted CD4+ cells. Staining is shown for CD25 vs. Foxp3 (upper row) and Foxp3 vs. CD49d (lower row). Numbers indicate percentage of cells in each gate.

Since CD49d is absent on the majority of Foxp3+ Treg cells, they can be significantly enriched by the depletion of CD49d+ cells from total CD4+ T cells. Human CD4+ T cells were depleted of all CD49d+ cells by MACS and analyzed for Foxp3 expression and compared to total CD4+ T cells. As shown in FIG. 7, Foxp3+ Treg can already be enriched up to 4-5 fold by the depletion of CD49d+ cells from human CD4+ T cells. Even more importantly, most of the cytokine producing cells are removed from this subset as cytokine secretion segregates with this marker (FIG. 6a).

EXAMPLE 9

Figure 2:
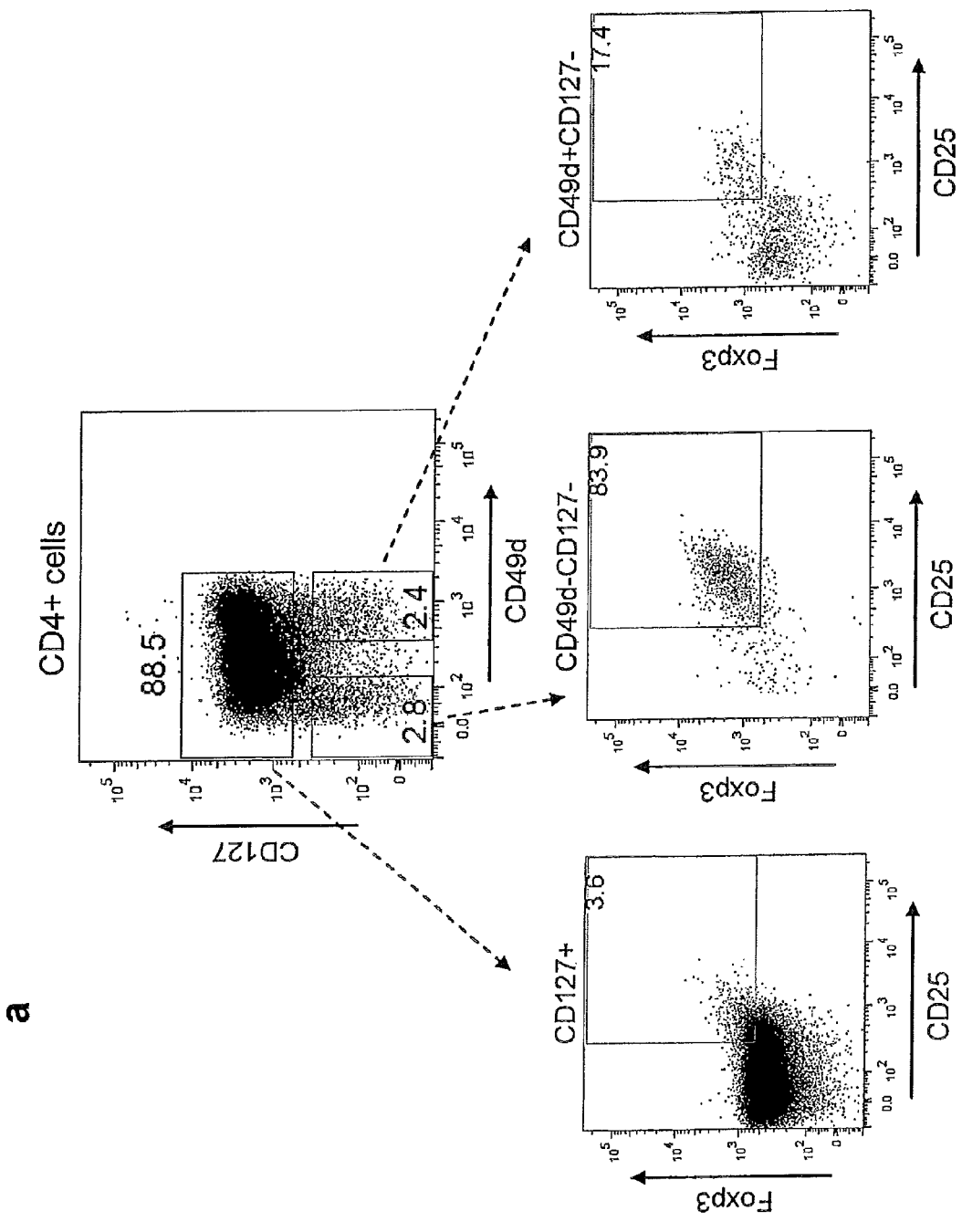
FIG. 2: CD49d discriminates Foxp3+ Treg cells from Foxp3−CD127− cells. a. Foxp3 expression in CD127/CD49d subsets of CD4+ T cells. Human PBMC were stained for CD4, CD25, CD127, CD49d and Foxp3 and gated for CD4+ cells. Upper panel: co-staining of CD49d and CD127. Gates and percentages of the three major populations are indicated. Lower panels: Co-staining of CD25 and Foxp3 is shown for CD127+ (left panel), CD49d−CD127− (middle panel) and CD49d+CD127− cells (right panel). Percentages represent the number of CD25+Foxp3+ Treg cells in the indicated quadrant. b. Isolation of CD49d−CD127− and CD49d+CD127− cells by FACS sorting. Untouched CD4+ cells isolated from PBMC with commercial MACS-depletion kit were stained with α-CD49d and α-CD127 (left panel) and sorted by FACS into the CD49d−CD127− (middle panel) and the CD49d+CD127− subset (right panel). Numbers indicate the fraction of cells in each quadrant. c. Suppressive capacity. Inhibition of the proliferative response by the two isolated cell subsets was determined in a FACS-based suppression assay as shown in FIG. 3b. Proliferation of CD4+ cells was induced by α-CD3 antibodies, suppressor cells were added at a ratio of 1:2. Suppression is expressed as '% inhibition' and was calculated by the fraction of dividing cells in reference to number of dividing α-CD3 stimulated CD4+ cells.
Figure 2:
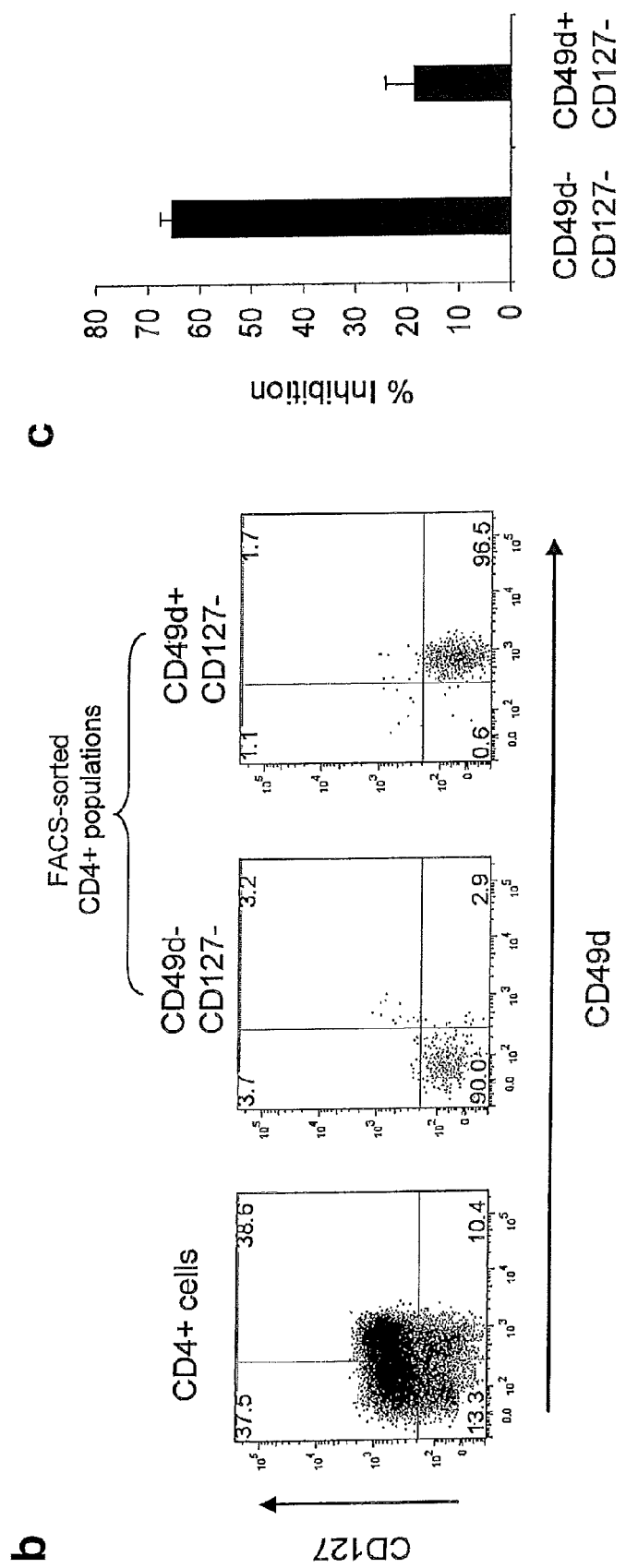

Depletion of CD49d+ Cells Removes Cytokine Producing CD4+ Effector Cells Contaminating CD127− Treg Preparations In combination with CD127, CD49d allows the isolation of untouched Treg cells (FIG. 2). Moreover, the segregation of CD49d with cytokine production also allows not only to remove Foxp3− cells but also the Th1- or Th17-like cells contaminating the CD127− Treg preparations. As shown in FIG. 8, activation of CD4+ cell subsets sorted according to their CD49d and CD127 expression clearly reveals that IFN-γ or IL-17 producing cells are absent from the CD49d−CD127− subset but present among the CD49d+CD127− subset.

Industrial Applicability

The method according to the present invention has the following advantages:

1) Safety. The regulations for reagents employed in human therapy are very strict. This applies particularly for the compounds administered during the treatment. Cells produced by positive sorting are carrying a foreign antibody on their surface. The inherent risk of antibodies is difficult to determine, and also 'humanization' does not necessarily prevent adverse effects, as documented recently in the dramatic failure of super-agonistic a-CD28 (Suntharalingam, G. et al. f N *Engl J Med* 355, 1018-28 (2006); Sharpe, A. H. & Abbas, A. K., N *Engl J Med* 355, 973-5 (2006)). This risk is avoided when untouched Treg cells are used that have: been purified only with depleting antibodies. Moreover, CD49d is present on potentially dangerous cytokine-secreting effector T cells but absent on Foxp3+ Treg cells. Hence, also the safety of conventionally obtained Treg cells can be increased by the removal of CD49d+ cells.

2) Viability and functional status of the cells. Another advantage untouched cells have compared to positively sorted cells as viability in vivo. Antibody-tagged cells are prone to depletion. Antibodies on the surface of cells can bind complement or, depending on the antibody subtype, attach to Fc-receptors on the surface of NK cells or macrophages. The outcome of this interaction is often cell death by complement-+mediated lyses or 'antibody dependent cell-mediated cyotoxicity' (ADCC). Binding of antibody-coated beads may also lead to formation of larger cell clusters that are eliminated by non-specific uptake mechanisms of the recipient. As a consequence, a significant fraction of the transferred cells may get eliminated before they can exhibit a beneficial effect. Moreover the binding of antibodies to cell surface receptors during purification may also alter the functional state. The molecule targeted during positive sorting of Treg cells is CD25. As α-chain of the IL-2 receptor it is vital for survival and function of Treg cells. Blocking may abrogate expansion and suppressor function (Thornton, A. M., Donovan, E. E., Piccirillo, C. A. & Shevach, E. M., *J Immunol* 172; 6519-23 (2004); Fontenot, J. 0., Rasmussen, J. P., Gavin, M. A. & Rudensky, A. Y., *Nat Immunol* 16, 1142-51 (2005); Kohm, A. P. et al., *J Immunol* 176, 3301-5 (2006); McNeill, A., Spittle, E. & Backstrom, B. T., *Scand J Immunol* 65, 63-9 (2007)), while cross-linking of the IL-2 receptor by antibodies, on the other hand, can lead to a premature activation (Barnard, A. L., Igakura, T., Tanaka, Y., Taylor, G. P. & Bangham, C. R., *Blood* 106, 988-95 (2005); von Bonin, A., Huhn, J. & Fleischer, B., *Immunol Rev* 161, 43-53 (1998)), potential complications that can simply be avoided when using untouched Treg cells.

3) Time & Costs. Compared to standard methods the new approach' is cost effective and fast. The CD49d/CD127 can be adapted to all common separation methods. For example, the method can be performed using only a single MACS column. Thus, isolation does not require expensive equipment and is faster and easier than conventional MACS-based methods.

4) Purity & GMP-compatibility. Flow cytometry based cell sorters are currently not approved for 'good manufacturing practice' (GMP). For clinical trials the isolation of donor cells has to be carried out by magnetic-bead technologies. First attempts to isolate Treg cells under GMP conditions, however, yielded an average purity of less than 50% (Hoffmann, P. et al., *Biol Blood Marrow Transplant* 12, 267-74 (2006)). Since the MACS purification was based on positive selection of CD25+ cells, the contaminating cells were mostly CD4+ CD25$^{low}$ effector and memory cells, posing an inherent risk to trigger GvHD when transferred into immune deficient patients. As a MACS-based method, the new approach is GMP compatible. Treg cells are obtained by a significantly higher degree of purity >70%, >80%, >90%, >95%, or even >98% with virtually no contaminating CD4+ effector cells. Moreover, the Treg cells are isolated untouched, which further improves compatibility of the procedure with GMP.

Accordingly, the method of the present invention offers a simple and cost effective way to isolate human Foxp3+ Treg cells. Additionally, the 'untouched' status of the cells, high purity and GMP compatibility of the method make the method widely applicable in different settings. The new method can therefore be employed to access 'untouched' human Treg cells for research & development, diagnosis and also offers a new perspective for their routine use for the manufacture of medicaments for immunotherapies.

Cited Literature

Fontenot, J. D. & Rudensky, A. Y. A well adapted regulatory contrivance: regulatory T cell development and the forkhead family transcription factor Foxp3. *Nat Immunol* 6, 331-7 (2005).

Sakaguehi, S. Naturally arising CD4+ regulatory t cells for immunologic self-tolerance and negative control of immune responses. *Annu Rev Immunol* 22, 531-62 (2004).

Baecher-Allan, C. & Hafler, D. A. Human regulatory T cells and their role in autoimmune disease. *Immunol Rev* 212, 203-16 (2006)

Robinson, D. S., Larche, M. & Durham, S. R. Tregs and allergic disease. *J Clin Invest* 114, 1389-97 (2004)

Roncarolo, M. G. & Battaglia, M. Regulatory T-cell immunotherapy for tolerance to self antigens and alloantigens in humans. *Nat Rev Immunol* 7, 585-98 (2007)

Hoffmann, P. et al. Isolation of CD4+CD25+ regulatory T cells for clinical trials. *Biol Blood Marrow Transplant* 12, 267-74 (2006)

Seddiki, N. et al. Expression of interleukin (IL)-2 and IL-7 receptors discriminates between human regulatory and activated T cells. *J Exp Med* 203, 1693-700 (2006)

Baecher-Allan, C., Brown, J. A., Freeman, G. J. & Hafler, D. A. CD4+CD25high regulatory cells in human peripheral blood. *J Immunol* 167, 1245-53 (2001).

Suntharalingam, G. et al. Cytokine storm in a phase 1 trial of the anti-CD28 monoclonal antibody TGN1412. *N Engl J Med* 355, 1018-28 (2006)

Liu, W. et al. CD127 expression inversely correlates with FoxP3 and suppressive function of human CD4+ Treg cells. *J Exp Med* 203, 1701-11 (2006).

Hori, S., Nomura, T. &. Sakaguchi, S. Control of regulatory T cell development by the transcription factor Foxp3. *Science* 299, 1057-61 (2003)

Mutis, T. et al. Human regulatory T cells control xenogeneic graft-versus-host disease induced by autologous T cells in RAG2-/-gammac-/-immunodeficient mice. *Clin Cancer Res* 12, 5520-5 (2006)

Sharpe, A. H. & Abbas, A. K. T-cell costimulation-biology, therapeutic potential, and challenges. *N Engl J Med* 355, 973-5 (2006)

Thornton, A. M., Donovan, E. E., Piccirillo, C. A. & Shevach, E. M. Cutting edge: IL-2 is critically required for the in vitro activation of CD4+CD25+ T cell suppressor function. *J Immunol* 172, 6519-23 (2004).

Fontenot, J., Rasmussen, J. P., Gavin, M. A. & Rudensky, A. Y. A function for interleukin 2 in Foxp3-expressing regulatory T cells. *Nat Immunol* 6, 1142-51 (2005).

Kohm, A. P. et al. Cutting Edge: Anti-CD25 monoclonal antibody injection results in the functional inactivation, not depletion, of CD4+CD25+ T regulatory cells. *J Immunol* 176, 3301-5 (2006).

McNeill, A., Spittle, E. & Backstrom, B. T. Partial depletion of CD69low-expressing natural regulatory T cells with the anti-CD25 monoclonal antibody PC61. *Scand J Immunol* 65, 63-9 (2007).

Barnard, A. L., Igakura, T. r Tanaka, Y., Taylor, G. P. & Bangham, C. R. Engagement of specific T-cell surface molecules regulates cytoskeletal polarization in HTLV-1-infected lymphocytes. *Blood* 106, 988-95 (2005).

von Bonin, A., Huhn, J. & Fleischer, B. Dipeptidyl-peptidase IV/CD26 on T cells: analysis of an alternative T-cell activation pathway. *Immunol Rev* 161, 43-53 (1998).

Randolph, D. A. & Fathman, C. G. Cd4+Cd25+ regulatory T cells and their therapeutic potential. *Annu Rev Med* 57, 381-402 (2006).

Tang, Q. & Bluestone, J. A. Regulatory T-cell physiology and application to treat autoimmunity. *Immunol Rev* 212, 217-37 (2006).

Masteller, E. L. et al. Expansion of functional endogenous antigen-specific CD4+CD25+ regulatory T cells from non-obese diabetic mice. *J Immunol* 175, 3053-9 (2005).

Waldmann, H. et al. Regulatory T cells and organ transplantation. *Semin Immunol* 16, 119-26 (2004).

Fontenot, J. D. et al. Regulatory T cell lineage specification by the forkhead transcription factor foxp3. *Immunity* 22, 32941 (2005).

Kleinewietfeld, M. et al. CCR6 expression defines regulatory effector/memory-like cells within the CD25(+)CD4+ T-cell subset. *Blood* 105, 2877-86 (2005).

Ebert, L. M. & McColl, S. R. Coregulation of CXC chemokine receptor and CD4 expression on T lymphocytes during allogeneic activation. *J Immunol* 166, 4870-8 (2001).

Sharpe, Methods of Cell Separation, Laboratory Techniques in Biochemistry and Molecular Biology, Vol. 18, ELSEVIER (1988)

Fisher, G. E. Francis, D. Rickwood (Eds.), Cell Separation: A Practical Approach, Oxford University Press (1999)

Allan S E, Crome S Q, Crellin N K, et al. Activation-induced FOXP3 in human T effector cells does not suppress proliferation or cytokine production. Int Immunol. 2007; 19:345-354.

Dieckmann et al. Ex vivo isolation and characterization of CD4(+)CD25(+) T cells with regulatory properties from human blood. *J Exp Med.* 193, 1303-10 (2001).

What is claimed is:

1. A method for isolating human Foxp3+ regulatory T cells by negative selection comprising
    (a) treating a sample containing (i) peripheral blood mononuclear cells, (ii) a lymphocyte containing fluid, or (iii) a lymphocyte containing tissue with antibodies, wherein said antibodies consist of an anti-CD49d antibody and an anti-CD127 antibody; and
    (b) depleting the sample of CD49+ and CD127+ cells via the anti-CD49d antibody and anti-CD127 antibody to obtain an enriched population of label- and antibody-free Foxp3+ regulatory T cells.

2. The method of claim 1, wherein at least one of the antibodies used in step (a) is labeled or immobilized.

3. The method of claim 1, wherein step (b) is carried out using centrifugation, cell elutriation, magnetic separation, fluorescence activated cell sorting, immunological separation, adhesion, complement lysis or flow cytometry.

4. The method of claim 1, wherein step (b) is carried out using magnetic cell separation, fluorescence activated cell sorting, or a column-based immunological separation.

5. A method for isolating human Foxp3+ regulatory T cells comprising
    (a) treating a sample containing (i) peripheral blood mononuclear cells, (ii) a lymphocyte containing fluid, or (iii) a lymphocyte containing tissue with antibodies, wherein said antibodies consist of an anti-CD49d antibody, an anti-CD25 antibody, and an anti-CD127 antibody;
    (b) depleting the sample of CD49+ and CD127+ cells using the anti-CD49d antibody and anti-CD127 antibody to obtain an enriched population of Foxp3+ regulatory T cells; and
    (c) selecting CD25+ cells to obtain a population of Foxp3+ regulatory T cells.

6. The method of claim 5, wherein at least one of the antibodies used in step (a) is labeled or immobilized.

7. The method of claim 5, wherein step (b) is carried out using centrifugation, cell elutriation, magnetic separation, fluorescence activated cell sorting, immunological separation, adhesion, complement lysis or flow cytometry.

8. The method of claim 5, wherein step (b) is carried out using magnetic cell separation, fluorescence activated cell sorting, or a column-based immunological separation.

* * * * *

UNITED STATES PATENT AND TRADEMARK OFFICE
CERTIFICATE OF CORRECTION

PATENT NO. : 9,213,028 B2  
APPLICATION NO. : 14/089179  
DATED : December 15, 2015  
INVENTOR(S) : Olaf Roetzschke et al.

Page 1 of 1

It is certified that error appears in the above-identified patent and that said Letters Patent is hereby corrected as shown below:

On the title page

At item (63), please delete "Continuation-in-part"  
At item (63), please insert --Continuation--

At item (30), please delete "07020026"  
At item (30), please insert --07020026.6--

At item (30), please delete "07024782"  
At item (30), please insert --07024782.0--

At item (30), please delete "08006864"  
At item (30), please insert --08006864.6--

At item (30), please delete "08008255"  
At item (30), please insert --08008255.5--

Signed and Sealed this  
Seventeenth Day of May, 2016

Michelle K. Lee  
*Director of the United States Patent and Trademark Office*